US012636402B2

(12) United States Patent 
Gannett et al.

(10) Patent No.: US 12,636,402 B2 
(45) Date of Patent: *May 26, 2026

(54) CHITOSAN DRESSING FOR CONTROL OF GASTROINTESTINAL BLEEDING

(71) Applicant: TRICOL BIOMEDICAL, INC., Portland, OR (US)

(72) Inventors: Cole Gannett, Portland, OR (US); Simon J. Mccarthy, Portland, OR (US); Ervelyn Winata, Portland, OR (US)

(73) Assignee: TRICOL BIOMEDICAL, INC., Portland, OR (US)

( * ) Notice: Subject to any disclaimer, the term of this patent is extended or adjusted under 35 U.S.C. 154(b) by 245 days.

This patent is subject to a terminal disclaimer.

(21) Appl. No.: 16/958,301

(22) PCT Filed: Dec. 28, 2018

(86) PCT No.: PCT/US2018/067995 
§ 371 (c)(1), 
(2) Date: Jun. 26, 2020

(87) PCT Pub. No.: WO2019/133898 
PCT Pub. Date: Jul. 4, 2019

(65) Prior Publication Data

US 2021/0052766 A1     Feb. 25, 2021

Related U.S. Application Data

(60) Provisional application No. 62/611,994, filed on Dec. 29, 2017.

(51) Int. Cl. 
*A61L 15/28*     (2006.01) 
*A61F 13/00*     (2024.01) 
(Continued)

(52) U.S. Cl. 
CPC .......... *A61L 15/28* (2013.01); *A61F 13/0289* (2013.01); *A61L 15/425* (2013.01); 
(Continued)

(58) Field of Classification Search 
None 
See application file for complete search history.

(56) References Cited

U.S. PATENT DOCUMENTS 7,371,403 B2     5/2008  McCarthy et al. 
7,482,503 B2     1/2009  Gregory et al. 
(Continued)

FOREIGN PATENT DOCUMENTS

CA         2669780 A1     5/2008 
CN       101018554 A     8/2007 
(Continued)

OTHER PUBLICATIONS

Ryu et al. "Bio-inspired adhesive catechol-conjugated chitosan for biomedical application: A mini review", Acta Biomaterial 27, 101-115 (Year: 2015).*

(Continued)

*Primary Examiner* — Isis A Ghali 
(74) *Attorney, Agent, or Firm* — Seed IP Law Group LLP

(57)          ABSTRACT

The present invention relates to a biocompatible, foldable, thin profile, low mass and high surface area, chitosan dressing, optionally modified with catechol, and suitable for treating bleeding in a physiological environment, e.g. gastrointestinal tract. The characteristics and structures of the chitosan dressing are provided. Methods of making and using the chitosan dressing are also provided.

19 Claims, 14 Drawing Sheets

(51) Int. Cl.

| | |
|---|---|
| *A61F 13/02* | (2024.01) |
| *A61L 15/42* | (2006.01) |
| *A61L 15/58* | (2006.01) |
| *C08B 37/08* | (2006.01) |

(52) U.S. Cl.

CPC ............ *A61L 15/58* (2013.01); *C08B 37/003* (2013.01); *A61F 2013/00463* (2013.01); *A61F 2013/00561* (2013.01); *A61L 2400/04* (2013.01)

(56) References Cited

U.S. PATENT DOCUMENTS

| | | | |
|---|---|---|---|
| 7,820,872 | B2 | 10/2010 | Gregory et al. |
| 7,897,832 | B2 | 3/2011 | McAdams et al. |
| 8,269,058 | B2 | 9/2012 | McCarthy et al. |
| 8,313,474 | B2 | 11/2012 | Campbell et al. |
| 8,741,335 | B2 | 6/2014 | McCarthy |
| 8,858,883 | B2 | 10/2014 | Dowling et al. |
| 8,920,514 | B2 | 12/2014 | Gregory et al. |
| 9,004,918 | B2 | 4/2015 | McAdams et al. |
| 9,204,957 | B2 | 12/2015 | Gregory et al. |
| 9,205,170 | B2 | 12/2015 | Lucchesi et al. |
| 10,086,105 | B2 | 10/2018 | Guo et al. |
| 10,315,023 | B2 | 6/2019 | Mantri et al. |
| 11,564,673 | B2 | 1/2023 | Perry et al. |
| 11,660,236 | B2 | 5/2023 | McCarthy et al. |
| 2004/0243043 | A1 | 12/2004 | McCarthy et al. |
| 2005/0038369 | A1 | 2/2005 | Gregory et al. |
| 2005/0137512 | A1 | 6/2005 | Campbell et al. |
| 2006/0089584 | A1 | 4/2006 | McAdams et al. |
| 2007/0166387 | A1 | 7/2007 | Ahuja et al. |
| 2008/0114286 | A1 | 5/2008 | Hamel et al. |
| 2008/0287907 | A1 | 11/2008 | Gregory et al. |
| 2009/0214712 | A1 | 8/2009 | Kang et al. |
| 2009/0226391 | A1 | 9/2009 | Roberts et al. |
| 2012/0065674 | A1 | 3/2012 | Levy |
| 2012/0296313 | A1 | 11/2012 | Andreacchi et al. |
| 2014/0193360 | A1 | 7/2014 | Lee et al. |
| 2015/0361218 | A1 | 12/2015 | Lee et al. |
| 2016/0030625 | A1 | 2/2016 | Mrozek et al. |
| 2018/0085500 | A1 | 3/2018 | Lee et al. |
| 2020/0306248 | A1 | 10/2020 | Beeley et al. |
| 2021/0052261 | A1 | 2/2021 | Perry et al. |
| 2021/0052766 | A1 | 2/2021 | Gannett et al. |
| 2021/0059867 | A1 | 3/2021 | Mccarthy et al. |
| 2021/0059868 | A1 | 3/2021 | Gannett et al. |
| 2021/0060203 | A1 | 3/2021 | Mccarthy et al. |
| 2023/0355224 | A1 | 11/2023 | Perry et al. |
| 2024/0009040 | A1 | 1/2024 | McCarthy et al. |

FOREIGN PATENT DOCUMENTS

| | | |
|---|---|---|
| CN | 101289477 A | 10/2008 |
| CN | 103189435 A | 7/2013 |
| CN | 104013990 A | 9/2014 |
| CN | 104619165 A | 5/2015 |
| CN | 105431176 A | 3/2016 |
| CN | 106334209 A | 1/2017 |
| CN | 107118357 A | 9/2017 |
| CN | 107375196 A | 11/2017 |
| CN | 111632026 A | 9/2020 |
| CN | 113209363 A | 8/2021 |
| CN | 115895440 A | 4/2023 |
| CN | 116540072 A | 8/2023 |
| EP | 2700419 A1 | 2/2014 |
| EP | 2778179 A2 | 9/2014 |
| EP | 3300669 A1 | 4/2018 |
| GB | 2 514 592 A | 12/2014 |
| JP | 2005503197 A | 2/2005 |
| JP | 2007516051 A | 6/2007 |
| JP | 2008525112 A | 7/2008 |
| JP | 2009502749 A | 1/2009 |
| JP | 2009513239 A | 4/2009 |
| JP | 2016138166 A | 8/2016 |
| JP | 2023516335 A | 4/2023 |
| KR | 20220161796 A | 12/2022 |
| WO | WO 9736630 A1 | 10/1997 |
| WO | WO 02102276 A2 | 12/2002 |
| WO | WO 2005062896 A2 | 7/2005 |
| WO | WO 2006071649 A2 | 7/2006 |
| WO | WO 2007009050 A2 | 1/2007 |
| WO | WO 2007139845 A2 | 12/2007 |
| WO | WO 2009111282 A2 | 9/2009 |
| WO | WO 2013180458 A1 | 12/2013 |
| WO | WO 2015175662 A1 | 11/2015 |
| WO | 2016112342 A1 | 7/2016 |
| WO | 2016159734 A1 | 10/2016 |
| WO | WO 2017161331 A1 | 9/2017 |
| WO | WO 2017214201 A1 | 12/2017 |
| WO | WO 2018204782 A1 | 11/2018 |

OTHER PUBLICATIONS

Sant et al. "Hybrid PGS-PCL microfibrous scaffolds with improved mechanical and biological properties", Journal of Tissue Eng Regen Med. April; 5(4): 283-291 (Year: 2011).*

Adler et al., "ASGE guideline: the role of endoscopy in acute non-variceal upper-GI hemorrhage," *Gastrointestinal Endoscopy* 60(4):497-504, 2004.

Banerjee et al., "The role of endoscopy in the management of patients with peptic ulcer disease," *Gastrointestinal Endoscopy* 71(4):663-668, 2010.

Boonpongmanee et al., "The frequency of peptic ulcer as a cause of upper-GI bleeding is exaggerated," *Gastrointestinal Endoscopy* 59(7):788-794, 2004.

Crooks et al., "Upper gastrointestinal haemorrhage and deprivation: a nationwide cohort study of health inequality in hospital admissions," *Gut* 61(4):514-520, 2012.

Elta et al., "Chapter 8: Approach to the patient with gross gastrointestinal bleeding," *Principles of Clinical Gastroenterology*:122-151, 2008.

Halkerston et al., "PWE-046 Early Clinical Experience of Endoclot™ in the Treatment of Acute Gastro-Intestinal Bleeding," *Gut* 62(Suppl 1):A149, 2013.

HCUP, "Diagnoses—Clinical Classification Software (CCS), Principal Diagnosis: # 153 Gastrointestinal hemorrhage," U.S. Department of Health and Human Services, 2014. (1 page).

Holster et al., "Hemospray in the treatment of upper gastrointestinal hemorrhage in patients on antithrombotic therapy," *Endoscopy* 45:63-66, 2013.

Jairath et al., "Mortality from Acute Upper Gastrointestinal Bleeding in the United Kingdom: Does It Display a "Weekend Effect"?," *Am J Gastroenterol* 106:1621-1628, 2011.

Jairath et al., "Prevalence, management, and outcomes of patients with coagulopathy after acute nonvariceal upper gastrointestinal bleeding in the United Kingdom," *Transfusion* 53:1069-1076, 2013.

Jairath et al., "Why do mortality rates for nonvariceal upper gastrointestinal bleeding differ around the world? A systematic review of cohort studies," *Can J Gastroenterol* 26(8):537-543, 2012.

Karaman et al., "Endoscopic Topical Application of Ankaferd Blood Stopper® in Gastrointestinal Bleeding," *The Journal of Alternative and Complementary Medicine* 18(1):65-68, 2012.

Kheirabadi et al., "Safety Evaluation of New Hemostatic Agents, Smectite Granules, and Kaolin-Coated Gauze in a Vascular Injury Wound Model in Swine," *The Journal of Trauma Injury, Infection and Critical Care* 68(2):269-278, 2010.

Peng et al., "Factors Associated With Failure of Initial Endoscopic Hemoclip Hemostasis for Upper Gastrointestinal Bleeding," *J Clin Gastroenterol* 40(1):25-28, 2006.

Rockey, "Gastrointestinal bleeding," *Gastroenterol Clin North Am* 34:581-588, 2005.

Ryu et al., "Catechol-Functionalized Chitosan/Pluronic Hydrogels for Tissue Adhesives and Hemostatic Materials", *Biomacromolecules* 12:2653-2659, 2011.

(56)  References Cited

OTHER PUBLICATIONS

Saraf et al., "Mechanical properties of soft human tissues under dynamic loading," *Journal of Biomechanics* 40:1960-1967, 2007.

Sheibani et al., "Natural history of acute upper GI bleeding due to tumours: short-term success and long-term recurrence with or without endoscopic therapy," *Aliment Pharmacol Ther* 38:144-150, 2013.

Sung et al., "Causes of Mortality in Patients With Peptic Ulcer Bleeding: A Prospective Cohort Study of 10,428 Cases," *Am J Gastroenterol* 105:84-89, 2010.

Sung et al., "Early clinical experience of the safety and effectiveness of Hemospray in achieving hemostasis in patients with acute peptic ulcer bleeding," *Endoscopy* 43:291-295, 2011.

Yau et al., "Safety and efficacy of Hemospray® in upper gastrointestinal bleeding," *Can J Gastroenterol Hepatol* 28(2):72-76, 2014.

Peng et al., "Factors Contributing to the Failure of Argon Plasma Coagulation Hemostasis in Patients with Nonvariceal Upper Gastrointestinal Tract Bleeding," *Hepato-Gastroenterology* 57:781-786, 2010.

Subramanian et al., "Mucus interaction to improve gastrointestinal retention and pharmacokinetics of orally administered nano-drug delivery systems," *Journal of Nanobiotechnology* 20:362, Aug. 6, 2022. (23 pages).

AUA Practice Guidelines Committee, "AUA Guideline on Management of Benign Prostatic Hyperplasia (2003). Chapter 1: Diagnosis and Treatment Recommendations," *The Journal of Urology* 170:530-547, Aug. 2003.

CGI Environment Variables, URL=https://hcup-us.ahrq.gov/reports/natstats/his96/clinclas.htm (1996), download date Sep. 30, 2022.

Elixhauser et al., "Hospital Inpatient Statistics, 1996," HCUP-3 Research Note. Agency for Health Care Policy and Research, Rockville, MD, URL=https://hcup-us.ahrq.gov/reports/natstats/his96/clinclas.htm (1996), download date Sep. 30, 2022.

Fitzpatrick JM, M.W., Minimally invasive and endoscopic management of benign prostatic hyperplasia. Campbell's Urology, 2002. 8th edition (Walsh PC editor)(Saunders): p. 1379-1422.

Hcup, National Statistics Trend Information 1993-2010 Transurethral Prostatectomy and Open Prostatectomy, 2010, US Department of Health and Human Services.

HCUP, NIS 2003 Means on Continuous Fields in Core File. HCUP Summary Statistics Report, 2003: p. 27-8.

Kavanagh et al., "Prevention and management of TURP-related hemorrhage," *Nature Reviews Urology* 8:504-514, Sep. 2011.

Kim et al., "Chitosan-catechol: A polymer with long-lasting mucoadhesive properties," *Biomaterials* 52:161-170, Feb. 2015.

McVary et al., "Update on AUA Guideline on the Management of Benign Prostatic Hyperplasia," *The Journal of Urology* 185:1793-1803, May 2011.

Roberts, Chapter 5, "Chemical Behaviour of Chitin and Chitosan," Chitin Chemistry, 1992. (10 pages).

Ryu et al., "Bio-Inspired, Water-Soluble to Insoluble Self-Conversion for Flexible, Biocompatible, Transparent, Catecholamine Polysaccharide Thin Films," *Adv. Funt. Mater.* 24:7709-7716, 2014.

Xu et al., "Mollusk Glue Inspired Mucoadhesives for Biomedical Applications," *Langmuir* 28:14010-14017, 2012.

Zeng et al., "Rapid in situ cross-linking of hydrogel adhesives based on thiol-grafted bio-inspired catechol-conjugated chitosan," *Biomaterials Processing* 32(5):612-621, 2017.

* cited by examiner

| Code # | Prototype | Layer | Test tube Test (mins) | Beaker Test (hours) | Fold-ability | In vivo screen #1 | In vivo screen #2 | In vivo screen #3 |
|---|---|---|---|---|---|---|---|---|
| A01 | 2Ch | N | | 0 | Y | | | |
| A02 | 2Ch | N | | 0 | Y | | | |
| A03 | 2Ch | N | | 0 | Y | | | |
| A04 | 4Ch | N | | >8 | Y | | | |
| A05 | 2ChGylcer | N | <15 | | | | | |
| A06 | 2Ch1cell | N | | 0 | Y | | | |
| A07 | 2Ch1Gel | N | | 1 | Y | N | N | |
| A08 | 10Gel | N | | | N | | | |
| A09 | 2PAA | N | | | N | | | |
| A10 | 1PAA | N | | 1 | Y | N | | |
| A11 | 2PAA | N | | 0 | N | | | |
| A12 | 0.3PAA | N | | | N | | | |
| B01 | 2Ch35DDA1 | N | <15 | | | | | |
| B02 | 2Ch35DDA2 | N | <15 | | | | | |
| B03 | 2Ch40DDA1 | N | <15 | | | | | |
| B04 | 2Ch40DDA2 | N | <15 | | | | | |
| C01 | 5Starch | N | <15 | | | | | |
| C02 | 3Pectin | N | <15 | | | | | |
| C03 | 3Guar | N | >60 | | | | | |
| C03-2 | 3Gu | N | | >7 | N | N | | |
| C04 | 3.5Gu | N | | 24 | N | | | |
| C05 | 2Gu1cel | N | | 0 | N | | | |
| C06 | 3Gu0.1Pol | N | | >4 | N | | | |
| C06-2 | 3Gu0.1Pol | N | | >4 | N | | | |
| C07 | 3.5Gu0.1Pol | N | | 23 | N | Y | | |

*FIG. 6A*

| Code # | Prototype | Layer | Test tube Test (mins) | Beaker Test (hours) | Fold-ability | In vivo screen #1 | In vivo screen #2 | In vivo screen #3 |
|---|---|---|---|---|---|---|---|---|
| D01 | 1Ch5Starch1 | N | <15 | 2 | N | | | |
| D02 | 1Ch1Pectin1 | N | <15 | | | | | |
| D03 | 1Ch1Guar1 | N | >60 | 2 | Y | | | |
| D04 | 1Ch5Starch2 | Y | <15 | | Y (cracks) | | | |
| D05 | 1Ch1Pectin2 | Y | <15 | | | | | |
| D06 | 1Ch1Guar1 | Y | >60 | 0.25/6-17 | Y (cracks) | | | |
| D07 | 4Ch2.5Gu | Y | | 0.25/6-23 | Y (cracks) | | | |
| D08 | 2Ch2.5Gu | Y | | 0.25/3-19 | Y (cracks) | | | |
| D09 | 4Ch2.5Gu | Y | | | Y (cracks) | | | |
| D10 | 2Ch2.5Gu | Y | | | Y (cracks) | | | |
| D11 | 2Ch1Gu | N | | | Y (cracks) | | | |
| D12 | 3Ch0.6Gu | N | | 3 | Y (cracks) | | | |
| D13 | 2Ch1.25Gu | N | | 3 | Y (cracks) | | | |
| D14 | 1Ch1.9Gu | N | | 2 | Y (cracks) | | | |
| D15 | 0.7Ch2.1Gu | N | | 2 | Y (cracks) | | | |
| D16 | 1.5Gu1Cat | N | | 2 | Y (cracks) | | | |
| D17 | 4Ch3Gu | N | | 3 | N | | | |
| D18 | 2Ch2Gu | N | | >5 | N | | | |
| D19 | 3Gu4Ch | Y | | 24 | Y (cracks) | N | | |
| D20 | 3Gu0.1Pol4Ch | Y | | 0 | Y | | | |
| D21 | 0.1PAA2Gu | N | | | Y (cracks) | | | |
| D22 | 1PAA3Gu | N | | 31 | N | N, N, N | | |
| D23 | 1PAA2Gu | N | | 48 | N | N | | |
| D24 | 4Ch0.1Pect | N | | 2-19 | Y | Y, N | Y, Y, Y, Y | N, Y, Y, N |

*FIG. 6B*

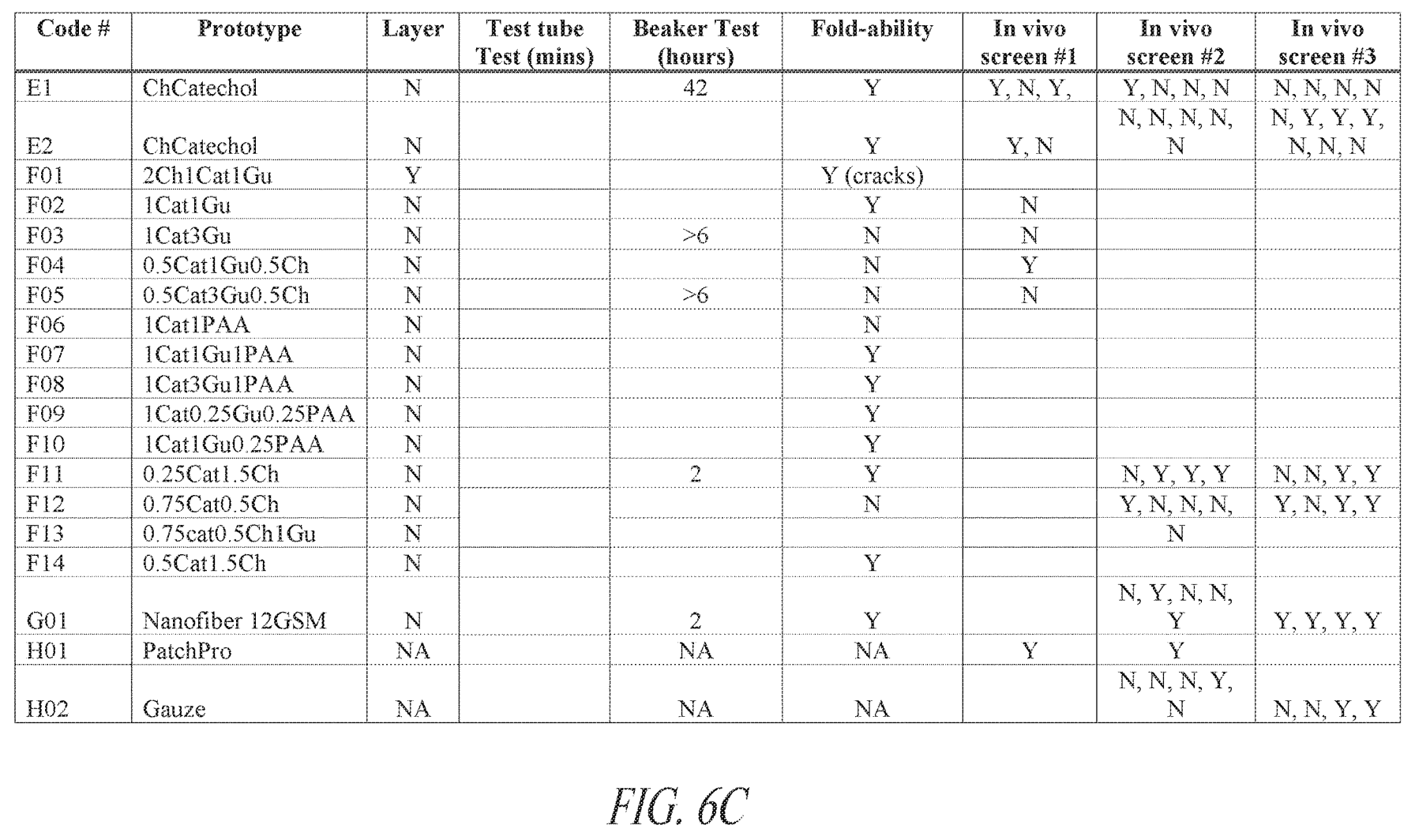

| Code # | Prototype | Layer | Test tube Test (mins) | Beaker Test (hours) | Fold-ability | In vivo screen #1 | In vivo screen #2 | In vivo screen #3 |
|---|---|---|---|---|---|---|---|---|
| E1 | ChCatechol | N | | | Y | Y, N, Y, | Y, N, N, N | N, N, N, N |
| E2 | ChCatechol | N | | 42 | Y | Y, N | N, Y, N, N, N | N, Y, Y, Y, N, N, N |
| F01 | 2Ch1Cat1Gu | Y | | | Y (cracks) | | | |
| F02 | 1Cat1Gu | N | | | Y | N | | |
| F03 | 1Cat3Gu | N | | >6 | N | N | | |
| F04 | 0.5Cat1Gu0.5Ch | N | | | N | Y | | |
| F05 | 0.5Cat3Gu0.5Ch | N | | >6 | N | N | | |
| F06 | 1CatPAA | N | | | N | | | |
| F07 | 1Cat1Gu1PAA | N | | | Y | | | |
| F08 | 1Cat3Gu1PAA | N | | | Y | | | |
| F09 | 1Cat0.25Gu0.25PAA | N | | | Y | | | |
| F10 | 1Cat1Gu0.25PAA | N | | | Y | | | |
| F11 | 0.25Cat1.5Ch | N | | 2 | Y | | N, Y, Y, Y | N, N, Y, Y |
| F12 | 0.75Cat0.5Ch | N | | | N | | Y, N, N, N | Y, N, Y, Y |
| F13 | 0.75cat0.5Ch1Gu | N | | | | | N | |
| F14 | 0.5Cat1.5Ch | N | | | Y | | | |
| G01 | Nanofiber 12GSM | N | | 2 | Y | | N, Y, N, N, Y | Y, Y, Y, Y |
| H01 | PatchPro | NA | | NA | NA | Y | Y | |
| H02 | Gauze | NA | | NA | NA | | N, N, N, Y, N | N, N, Y |

*FIG. 6C*

| Code # | Prototype | % Chitosan | Chitosan Lot | % Acetic Acid | %DDA | % Chitosan Catechol | Catechol Approach | %PAA | %Starch | %Pectin | %Guar | Mixture | Layer | Chitin microfiber | Notes 1 |
|---|---|---|---|---|---|---|---|---|---|---|---|---|---|---|---|
| A01 | 2Ch | 2 | A | 2 | 80 | | | | | | | | | | |
| A02 | 2Ch | 2 | B | 1 | 95 | | | | | | | | | | |
| A03 | 2Ch | 2 | B | 2 | 95 | | | | | | | | | | |
| A04 | 4Ch | 4 | B | 2 | 95 | | | | | | | | | | |
| A05 | 2ChGylcer | 2 | A | 2 | 40 | | | | | | | | | | +2% glycerol |
| A06 | 2Ch1cell | 2 | A | 1 | 80 | | | | | | | | Yes | | | 1%cellulose |
| A07 | 2Ch1Gel | 2 | A | 1 | 80 | | | | | | | | Yes | | | 1% Gelatin |
| A08 | 10Gel | | | | | | | | | | | | | | | 10% Gelatin |
| A09 | 2PAA | | | | | | | 2 | | | | | | | | |
| A10 | 1PAA | | | | | | | 1 | | | | | | | | |
| A11 | 2PAA | | | | | | | 2 | | | | | | | | |
| A12 | 0.3PAA | | | | | | | 0.25 | | | | | | | | |
| B01 | 2Ch35DDA1 | 2 | A | 2 | 35 | | | | | | | | | Yes | 0.1% chitin |
| B02 | 2Ch35DDA2 | 2 | A | 2 | 35 | | | | | | | | | | |
| B03 | 2Ch40DDA1 | 2 | A | 2 | 40 | | | | | | | | | Yes | 0.1% chitin |
| B04 | 2Ch40DDA2 | 2 | A | 2 | 40 | | | | | | | | | | |
| C01 | 5Starch | | | | | | | | 5 | | | | | | single polymer |
| C02 | 3Pectin | | | | | | | | | 3 | | | | | single polymer |
| C03 | 3Guar | | | | | | | | | | 3 | | | | single polymer |
| C03-2 | 3Gu | | | | | | | | | | 3 | | | | |
| C04 | 3.5Gu | | | | | | | | | | 3.5 | | | | |
| C05 | 2Gu1cel | | | | | | | | | | 2 | Yes | | | 1% cellulose |
| C06 | 3Gu0.1Pol | | | | | | | | | | 3 | Yes | | | 0.1 Polox |
| C06-2 | 3Gu0.1Pol | | | | | | | | | | 3 | Yes | | | 0.1% Polox |
| C07 | 3.5Gu0.1Pol | | | | | | | | | | 3.5 | Yes | | | 0.1% Polox |

*FIG. 8A*

| Code # | Prototype | % Chitosan | Chitosan Lot | % Acetic Acid | %DDA | % Chitosan Catechol | Catechol Approach | %PAA | %Starch | %Pectin | %Guar | Mixture | Layer | Chitin microfiber | Notes 1 |
|---|---|---|---|---|---|---|---|---|---|---|---|---|---|---|---|
| D01 | 1Ch5Starch1 | 1 | A | 1 | 80 | | | | 5 | | | Yes | | | |
| D02 | 1Ch1Pectin1 | 1 | A | 1 | 80 | | | | | 1 | | Yes | | | |
| D03 | 1Ch1Guar1 | 1 | A | 1 | 80 | | | | | | 1 | Yes | | | |
| D04 | 1Ch5Starch2 | 1 | A | 1 | 80 | | | | 5 | | | | Yes | | |
| D05 | 1Ch1Pectin2 | 2 | A | 2 | 80 | | | | | 1 | | | Yes | | |
| D06 | 1Ch1Guar1 | 2 | A | 2 | 80 | | | | | | 1 | | Yes | | |
| D07 | 4Ch2.5Gu | 4 | B | 2 | 95 | | | | | | 2.5 | | Yes | | |
| D08 | 2Ch2.5Gu | 2 | B | 2 | 95 | | | | | | 2.5 | | Yes | | |
| D09 | 4Ch2.5Gu | 4 | B | 2 | 95 | | | | | | 2.5 | | Yes | | |
| D10 | 2Ch2.5Gu | 2 | B | 2 | 95 | | | | | | 2.5 | | Yes | | ↑guar layer |
| D11 | 2Ch1Gu | 2 | B | 2 | 95 | | | | | | 1.25 | Yes | | | |
| D12 | 3Ch0.6Gu | 3 | B | 2 | 95 | | | | | | 0.625 | Yes | | | |
| D13 | 2Ch1.25Gu | 2 | B | 2 | 95 | | | | | | 1.25 | Yes | | | |
| D14 | 1Ch1.9Gu | 1 | B | 2 | 95 | | | | | | 1.875 | Yes | | | |
| D15 | 0.7Ch2.1Gu | 0.68 | B | 2 | 95 | | | | | | 2.075 | Yes | | | |
| D16 | 1.5Gu1Cat | | B | | | 1 | 1 | | | | 1.5 | Yes | | | |
| D17 | 4Ch3Gu | 4 | B | 2 | 95 | | | | | | 3 | Yes | | | |
| D18 | 2Ch2Gu | 2 | A | 2 | 80 | | | | | | 2 | Yes | | | |
| D19 | 3Gu4Ch | 4 | B | 2 | 95 | | | | | | 3 | Yes | Yes | | |
| D20 | 3Gu0.1Pol4Ch | 4 | B | 2 | 95 | | | | | | 3 | Yes | Yes | | Gu+0.1% Polox |
| D21 | 0.1PAA2Gu | | | | | | | 0.07 | | | 2.21 | Yes | | | |
| D22 | 1PAA3Gu | | | | | | | 1 | | | 3 | Yes | | | |
| D23 | 1PAA2Gu | | | | | | | 1 | | | 2 | Yes | | | |
| D24 | 4Ch0.1Pect | 4 | B | 2 | 95 | | | | | | | Yes | | | 0.1 Pectin |
| E01 | ChCatechol | | | | | 1 | 2 | | | | | | | | |
| E02 | ChCatechol | | | | | 1 | 3 | | | | | | | | |

*FIG. 8B*

| Code # | Prototype | % Chitosan | Chitosan Lot | % Acetic Acid | %DDA | % Chitosan Catechol | Catechol Approach | %PAA | %Starch | %Pectin | %Guar | Mixture | Layer | Chitin microfiber | Notes 1 |
|---|---|---|---|---|---|---|---|---|---|---|---|---|---|---|---|
| F01 | 2Ch1Cat1Gu | 2 | B | 2 | 95 | 1 | 3 | | | | 2.5 | | Yes | | |
| F02 | 1Cat1Gu | | | | | 1 | 1 | | | | 1 | Yes | | | |
| F03 | 1Cat3Gu | | | | | 1 | 1 | | | | 3 | Yes | | | |
| F04 | 0.5Cat1Gu0.5Ch | 0.5 | A | 1 | 80 | 0.5 | 1 | | | | 1 | Yes | | | |
| F05 | 0.5Cat3Gu0.5Ch | 0.5 | A | 1 | 80 | 0.5 | 1 | | | | 3 | Yes | | | |
| F06 | 1Cat1PAA | | | | | 1 | 1 | 1 | | | | Yes | | | |
| F07 | 1Cat1Gu1PAA | | | | | 1 | 1 | 1 | | | 1 | Yes | | | |
| F08 | 1Cat3Gu1PAA | | | | | 1 | 1 | 1 | | | 3 | Yes | | | |
| F09 | 1Cat0.25Gu0.25PAA | | | | | 1 | 1 | 0.25 | | | 0.25 | Yes | | | |
| F10 | 1Cat1Gu0.25PAA | | | | | 1 | 1 | 0.25 | | | 1 | Yes | | | |
| F11 | 0.25Cat1.5Ch | 1.5 | A | 1 | 80 | 0.25 | 2 | | | | | Yes | | | |
| F12 | 0.75Cat0.5Ch | 0.5 | A | 1 | 80 | 0.75 | 1 | | | | | Yes | | | |
| F13 | 0.75cat0.5Ch1Gu | 0.5 | A | 1 | 80 | 0.75 | 3 | | | | 1 | Yes | | | |
| F14 | 0.5Cat1.5Ch | 1.5 | A | 2 | 80 | 0.5 | 3 | | | | | Yes | | | |
| G01 | Nanofiber 12GSM | | | | | | | | | | | | | | |

*FIG. 8C*

CHITOSAN DRESSING FOR CONTROL OF GASTROINTESTINAL BLEEDING

GOVERNMENT LICENSE RIGHTS

This invention was made with Government support under R44DK104564 awarded by National Institute of Diabetes and Digestive and Kidney Disease. The Government has certain rights in the invention.

BACKGROUND

Technical Field

This disclosure relates to the field of chitosan materials comprising catechol modified chitosan and uses thereof.

Description of the Related Art

Prolonged bleeding, with its associated risks in mortality and morbidity, remains a serious problem in the gastrointestinal (GI) tract. Techniques and devices that could provide for rapid bleeding control in gastrointestinal bleeding (GIB) for both upper gastrointestinal bleeding (UGIB) and lower gastrointestinal bleeding (LGIB) are needed. Although there have been advances in bleeding control using advanced dressings for applications outside of GIB bleeding none of these advances have yet translated to the unique conditions of the gastrointestinal tract and especially the upper gastrointestinal tract where delivery, adhesion, enzyme activity and acidity considerations are highly challenging.

Gastrointestinal bleeding (GIB) is a common presentation to the emergency department. According to the U.S. Department of Health and Human Service, from 2000 to 2014, there was an average of over 350,000 discharges from gastrointestinal hemorrhage annually. In the U.S., the direct hospital cost in 2010 due to GIB exceeded $1.1 billion [1]. Upper GIB (UGIB), defined as gastrointestinal bleeding proximal to the ligament of Treitz, is approximately five times more common than lower GIB (LGIB) [2]. Acute UGIB is a potentially life-threatening emergency that necessitates prompt assessment, resuscitation and appropriate medical and endoscopic management. Despite recent advances in management of GIB in western countries, the mortality rate of acute UGIB has not significantly improved, and remains as high as 10-14% [3, 4]. The major cause of death after GIB is death secondary to cardiorespiratory complications, which is not surprising given the burden of comorbidities in such patients; death due to uncontrollable hemorrhage is reported to account for between 20% and 25% of cases [5, 6]. While little can be done to correct comorbidities urgently, more effective and rapid bleeding control will allow significant reductions in the incidence of UGIB related morbidity and mortality. In general, the most common causes of acute UGIB are peptic ulcers, gastroesophageal varices, Mallory-Weiss tears and erosive esophagogastritis [7]. Nonvariceal upper gastrointestinal bleeding (NVUGIB) encompasses all causes of UGIB except bleeding esophageal or gastric varices. The incidence of peptic ulcer disease has decreased because of the development and utilization of proton pump inhibitors as well as the identification, treatment and eradication of *Helicobacter pylori* in individual patients [8]. Despite decreased peptic ulcer incidence, mortality among NVUGIB patients ranges from 3-4% [9]. While rarely life threatening, gastric malignancies can lead to friable tissue with diffuse bleeding that is difficult to address with traditional physical hemostatic methods (clips, bands, ligation) or cautery [10].

Current endoscopic management of patients with acute UGIB includes thermal therapy (e.g., bipolar electrocoagulation, heater probe, monopolar electrocoagulation, argon plasma coagulation, and laser), injection (epinephrine, sclerosants (e.g., absolute ethanol, polidocanol, and ethanolamine)), thrombin or fibrin glue (thrombin plus fibrinogen)), and clips [11, 12].

In general, the majority of patients with bleeding peptic ulcers, hemostasis is achieved with combination of the above endoscopic therapeutic modalities. However, there remains a subset of patients, approximately 5%, in which endoscopic treatments are not sufficient for hemostasis and thus require interventional radiology or surgical interventions [13, 14].

Endoscopic therapy fails for a variety of reasons including poor visibility of lesion due to active pulsating bleeding, difficult anatomic location of lesion for endoscopy, maximal therapy with currently available tools, and severe coagulopathy. Only available outside the United States, three different spray-based, hemostatic powder devices, Ankeford Blood Stopper [15], EndoClot™ [16] and HemoSpray™ [17-19] are also being considered to control NVUGIB. A potential concern with Hemospray is that it is a related product to WoundStat™ which was withdrawn in 2009 in the United States due to its pro-clotting nanoparticulate bentonite promoting diffuse micro-emboli [20] that could cause tissue necrosis and organ failure.

BRIEF SUMMARY

Although existing tools in the United States readily control a significant portion of UGIB, there remains unmet need for the low risk device of the subject invention that provides rapid control of brisk arterial bleeding. Broad application of the subject invention will enable significant reduction in morbidity and mortality in gastrointestinal bleeding treatment with concomitant reduction in associated health care expenditure.

The subject chitosan gastrointestinal hemostatic dressing (CGHD) of the invention is amenable to use in all gastrointestinal bleeding applications and may be delivered by, for example, wire through a standard endoscopic working channel (≤3.2 mm diameter) or by balloon catheter delivery. The subject CGHD invention will provide an opportunity to address or mitigate deficiencies with current modalities, such as clipping, thermal coagulation and injection, which necessitate pinpoint accuracy and which is challenging under impaired visibility of brisk bleeding conditions.

The present invention comprises compositions, methods of using the compositions, and methods of making the compositions.

In certain embodiments, the chitosan dressing comprising a catechol modified chitosan, wherein the dressing is hemostatic and has a thickness that is 500 microns or less. The dressing may have a dry dressing thickness that is one of: (i) about 200 microns or less; (ii) about 100 microns or less; or (iii) about 50 microns or less. The dressing may have a density that is in the range of about 0.03 g/cm³ to about 0.7 g/cm³, in the range of: (i) about 0.3 g/cm³ to about 0.4 g/cm³; (ii) about 0.4 g/cm³ to about 0.5 g/cm³, or in the range of about 0.35 g/cm³ to about 0.55 g/cm³. The dressing may be compressed. The dressing may be square, rectangular, circular, or circular petal shaped and measurements, for each of the length and width for a square or rectangular shape, may range from about 10 mm to about 50 mm, or for a circular or circular petal shape from about 10 mm to about 50 mm in diameter. In certain embodiments, the dressing measures as one of: (i) 10 mm by 10 mm; (ii) 20 mm by 20 mm; or (iii) 25 mm by 25 mm. The dressing, when dry, has a moisture content of: (1) 15% or less by weight (w/w); (2) 8% or less by weight (w/w); or (3) 4% or less by weight (w/w). The dressing may have an adhesive side and a non-adhesive side. The dressing may have an adhesive side provided on a first layer and a non-adhesive side is provided on a second layer. The adhesive side of the dressing adheres to a tissue surface when the dressing is wet. The non-adhesive side of the dressing does not adhere to a delivery device when the dressing is wet. The dressing can adhere to a gastrointestinal mucosa in 1 minute or less. The dressing can form a quaternary ammonium cation at the chitosan glucosamine C-2 amine at a tissue site. The dressing may comprise catechol oxidized to o-quinone and cross-linked in the chitosan dressing. The chitosan dressing may have a brown coloration, including a dark brown coloration. In one embodiment, the dressing may comprise catechol that is not oxidized, and wherein the chitosan dressing has a pink coloration. The dressing may comprise freeze-dried lamella. The dressing may comprise a freeze-dried structure has a thickness of 50 microns or less. The dressing may comprise a freeze-dried structure that includes more than one freeze-dried layer. The dressing may comprise spun fibers. The dressing may comprise a porous surface. The dressing may comprise a porous surface wherein the porous surface provides one or more of: (i) and absorbent surface; and (ii) channels to redirect moisture away from a target tissue surface site. The dressing may adhere to wet tissue when in a wet condition. The dressing adherence strength may be greater than or equal to about 1 kPa. The dressing resists dissolution in water, saline solution, blood, or GI fluid at about 37° C. for at least about 6 hours. The dressing can be folded or furled without cracking or tearing. The dressing may, in an open, unfurled, or unfolded condition, have an outward facing surface area that is one of about six times greater, about five times greater, or about four times greater than the outward facing surface area of that same dressing when it is in a closed, furled, or folded condition. The dressing may have a ratio of the outward facing surface area of an open, unfurled, or unfolded condition relative to a closed, furled, or folded condition that is about 15:1, or about 14:1, or about 13:1, or about 12:1, or about 11:1, or about 10:1, or about 9:1, or about 8:1, or about 7:1, or about 6:1, or about 5:1, or about 4:1, or about 3:1, or about 2:1. The dressing can be punctured or sewn without cracking or tearing. The dressing can be cross-linked. The dressing is able to be delivered intact by a balloon device, a wire device, or an endoscopic device, wherein said device may comprise a working channel having a diameter of 3.2 mm or less, and wherein the dressing is delivered through the working channel. The dressing is able to wet and adhere intact to gastric mucosa in less than 30 seconds with application of light pressure, e.g., about 200-300 g. The dressing is able to remove hydrophilic and hydrophobic biological fluids that can interfere with adhesion. The dressing is able to stay in place intact and stop moderate to oozing bleeding ranging from between about 20 ml/min to about 150 ml/min. The dressing readily detaches from a delivery device after adherence to a target tissue site. The dressing is able to resist dissolution for at least six hours after adhering to an injury site in presence of corrosive enzymes and acid environment of about pH 3. The dressing is able to seal and protect a target tissue site for at least 12 hours. The dressing is able to achieve a controlled, slow dissolution from the attachment site over a period of time not exceeding seven (7) days. The dressing is able to be folded and unfolded. The dressing is able to be furled and unfurled. The dressing is not readily soluble in water, saline solution, blood, or GI fluid at about 37° C. for at least 12 hours following application. The dressing is not readily soluble in water, saline solution, blood, or GI fluid at about 37° C. for at least 24 hours following application. The dressing does not adhere to a delivery device. The dressing does not does not increase or decrease in size by more than about 25% in length and width, or more than about 50% in thickness in the presence of water, saline solution, blood, or GI fluid at about 37° C. The dressing comprises an adhesive side that interacts with an injury site, and wherein the chitosan dressing comprises a non-adhesive side that interacts with one of a delivery device or the adhesive side when the dressing is in a dry and folded or a dry and furled condition. The dressing is capable of being terminally sterilized without affecting dressing characteristics. The chitosan dressing is capable of being stored under controlled conditions over time without affecting dressing characteristics.

UGIB bleed rates, or blood flow rates, in ml/min suitable for treatment by the devices described herein may range from about 1 ml/min to about 200 ml/min. In preferred embodiments, the bleeding rates addressed by the devices range from about 1 ml/min to about 150 ml/min. A Forrest 1a UGIB is about 25 ml/min. For subjects suffering a bleed rate of much greater than a Forrest 1a, survival is unlikely unless they are already in an operating theater. UGIB bleed rate of between about 20 ml/min and 25 ml/min is considered "brisk" bleeding. Oozing bleeding is generally greater than about 1 ml/min as it is noted that low bleeding rates such as 1 ml/min typically clot and stop of their own accord unless the subject is on anticoagulation therapy or has a disorder of the clotting cascade due to reasons other than taking anticoagulation medication. For such a subject with irreversible anticoagulation medication or with a bleeding disorder, 1 ml/min oozing bleeding remains concerning and needs to be addressed such as by the device of the invention. In some embodiments, the devices described herein are used to address UGIB bleeding rates of between about 1 ml/min and about 25 ml/min, or about 1 ml/min and about 20 ml/min, or about 1 ml/min and about 15 ml/min, or about 1 ml/min and about 10 ml/min, or about 1 ml/min and about 5 ml/min. In some embodiments, the dressing can be used for treatment of a disease, condition, disorder, trauma, or injury. For example, the use of the dressing in the treatment of a disease, condition, disorder, trauma, or injury, comprising directly adhering the dressing at an injury site upon wetting, and applying pressure to the dressing for about 30 seconds. The dressing for use in treatment of a disease, condition, disorder, trauma, or injury, may remove hydrophilic and hydrophobic biological fluids upon adherence. The dressing for use in treatment of a disease, condition, disorder, trauma, or injury, may comprise leaving the dressing in place at a target tissue site and the dressing may remain at the target tissue site for at least 24 hours. The dressing for use in treatment of a disease, condition, disorder, trauma, or injury, may be capable of slow dissolution at the target tissue site and dissolves completely without human intervention in seven days or less.

In some embodiments, the invention disclosed herein comprises methods of producing the chitosan dressing. In one embodiment, the method comprises: performing synthesis with chitosan and catechol in an aqueous reaction solution; maintaining a pH of the reaction solution at or below pH 5.5; increasing the pH of the reaction solution, and controlling oxygen exposure to the reaction solution, to provide catechol oxidation and cross-linking; and drying the reaction solution. In certain embodiments, the methods do not comprise an intermediate drying step between step. In certain embodiments, the methods comprise increasing the pH of the reaction solution from about 5.8 to about 6.2. Another embodiment of a method of producing the chitosan dressing comprises a method of producing a chitosan dressing comprising: freeze-drying a first aqueous solution comprising chitosan; freeze-drying a second aqueous solution comprising chitosan; obtaining a low-density chitosan dressing with inter-connected porous structure from each of the above steps; and compressing the low-density chitosan dressing from each of steps; and preparing a two-layer chitosan dressing from the compressed low-density chitosan dressing. In certain embodiments, the low-density chitosan dressings from each of above-mentioned freeze-drying steps are combined prior to compression. In certain embodiments, the compressing of step may occur at temperature ranging from about 20° C. to about 150° C. In certain embodiments, the dressing is dried to a moisture content of less than about 15% (w/w).

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF THE SEVERAL VIEWS OF THE DRAWINGS

FIGS. 6A-6C depict a table showing dissolution testing results.

FIGS. 8A-8C depict a table showing formulation approaches, hydrophilic polymers, and % w/w of solution hydrophilic polymer components.

DETAILED DESCRIPTION

Figure 1:
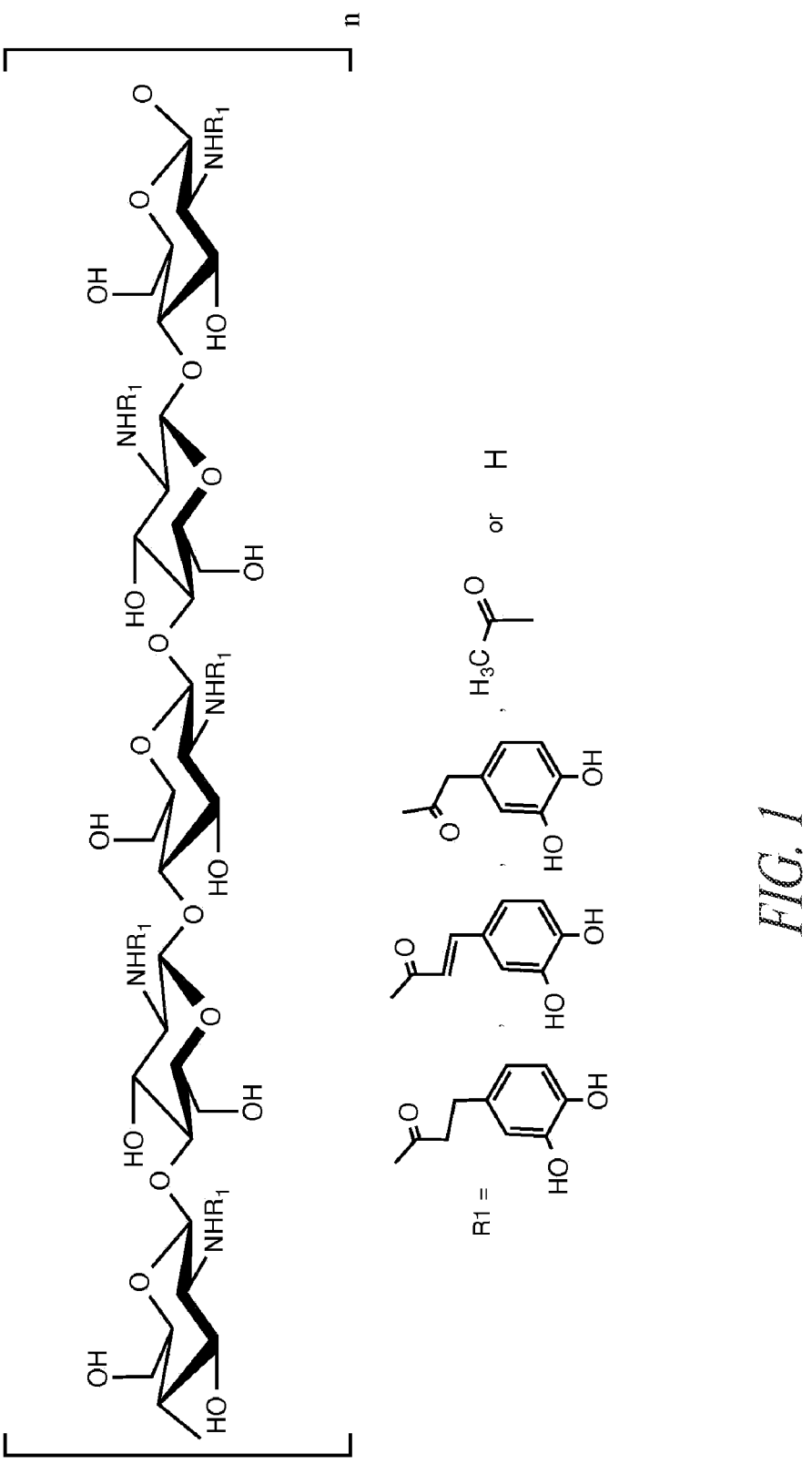
FIG. 1 depicts a chemical structure representation of chitosan (R1=H and acetyl radical) and catechol modified chitosan (R1=H, acetyl, hydrocaffeic acid radical, caffeic acid radical, trans-caffeic acid radical and Homoprotocatechuic acid radical). For chitosan polymer, preferably n>60, more preferably n>300, and most preferably n>600.

The present invention relates to a biocompatible, foldable, thin profile, chitosan-based dressing comprising catechol modified chitosan and characterized by one or more, or all, of the following features, such that it is: (1) able to be delivered intact by balloon or through endoscopic device; (2) is able to wet and adhere intact to gastric mucosa in under 30 seconds with application of light pressure; (3) has capillarity, porosity and absorbency that is able to remove hydrophilic and hydrophobic biological fluids that can interfere with adhesion; (4) is able to stay in place intact and stops moderate to oozing bleeding, e.g., a bleeding rate of between about 20 ml/min to about 100 ml/min, or greater; (5) is able to be released from the delivery device to allow withdrawal of the delivery device from the GI environment; (6) is able to resist detrimental rapid breakdown (<6 hours) in the corrosive enzymes and acidity (≥pH 3) of the GI environment; (7) is able to protect the gastrointestinal injury site for preferably up to 12 hours, more preferably up to 24 hours and most preferably up to 96 hours to assist with its subsequent acute healing and closure; and (8) is able to achieve a controlled, slow dissolution from the attachment site to allow for unassisted complete removal in less than seven days with the dissolved residue passing safely through the alimentary tract.

Chitosan Dressing

Chitosan dressings may refer to compositions that include varying amounts of chitosan. The general contents, general chemical compositions and different forms of a chitosan dressing are described, for example, in U.S. Pat. Nos. 7,820,872, 7,482,503, 7,371,403, 8,313,474, 7,897,832, 9,004,918, 8,920,514, 9,204,957, 8,741,335, 8,269,058, 9,205,170, and 10086105. Such chitosan dressings, due to their chemical and physical properties as described previously, have been used to stop bleeding.

The chitosan used preferably comprises the non-mammalian material poly [.beta.-(1.fwdarw.4)-2-amino-2-deoxy-D-glucopyranose. The chitosan can be processed in conventional ways from chitin obtained, for example, from animal crustacean shells such as shrimp. Chitosan may be biocompatible and biodegradable within the body, and is capable of being broken down into glucosamine, a benign material. The catechol-modified chitosan used herein may include reference to catechol-added chitosan.

A chitosan dressing can be dry or wet. A chitosan dressing is "dry" if the moisture content in the chitosan dressing is less than about 15% by weight, preferably about 10% by weight, and more preferably about 5% by weight. A chitosan dressing is "wet" when the chitosan dressing has come in contact with a source of water, including water in a physiological environments and biological fluids, or in an aqueous solution. For example, a chitosan dressing becomes wet when the chitosan dressing, as described in this disclosure, comes in contact with gastrointestinal tract fluid or a gastrointestinal tract tissue surface (covered by gastrointestinal mucosa). The chitosan dressing, remaining substantially in a solid form absorbs, displaces, redirects or channels water/moisture in the physiological environment of gastrointestinal tract in amounts sufficient to permit adhesion of the chitosan dressing to the tissue surface. The adhered chitosan dressing can be used to seal wound surfaces and slow or stop further bleeding.

In a preferred embodiment, the chitosan gastrointestinal hemostatic dressing of the invention contains preferably greater than or equal to 25% by weight chitosan; more preferably greater than or equal to 50% by weight chitosan and most preferably greater than or equal to 75% by weight chitosan. Chitosan is a generic term used to describe linear polysaccharides that are composed of glucosamine and N-acetyl glucosamine residues joined by $\beta$-(1-4) glycosidic linkages (typically the number of glucosamines $\geq$N-acetyl glucosamines) and whose composition is soluble in dilute aqueous acid (Roberts 1991). The chitosan family encompasses poly-$\beta$-(1-4)-N-acetyl-glucosamine and poly-$\beta$-(1-4)-N-glucosamine with the acetyl residue fraction and its motif decoration (either random or block) affecting chitosan chemistry. The C-2 amino group on the glucosamine ring in chitosan allows for protonation, and hence solubilization of chitosan in water (pKa$\approx$6.5) (Roberts 1991). Other hydrophilic polymers such as, for example, guar, pectin, starch and polyacrylic acid may be used.

In a preferred embodiment, the dressing of the invention is polymeric, thin (preferably dry dressing thickness of about $\leq$500 microns, more preferably thickness of about $\leq$200 microns, most preferably thickness of about $\leq$100 microns), flexible, porous, dry, biocompatible, tissue adherent and hemostatic.

The dressings are not limited in shape, however square, rectangular, circular, or circular petal shaped dressings are preferred. In one embodiment, a maximum size could be up to about 50 mm×50 mm square or 50 mm in diameter. In another embodiment, dressing size could be about 45 mm×45 mm square or 45 mm in diameter, 40 mm×40 mm square or 40 mm in diameter, 35 mm×35 mm square or 35 mm in diameter, 30 mm×30 mm square or 30 mm in diameter, 25 mm×25 mm square or 25 mm in diameter, 15 mm×15 mm square or 15 mm in diameter, 10 mm×10 mm square or 10 mm in diameter, etc. In still another embodiment, each of the length and width may range from about 10 mm to about 50 mm, or from about 10 mm to about 50 mm in diameter. As dressings become larger in size they become increasingly subject to delivery limitations in confined cavities such as the stomach, etc.

Dressings described herein may provide a large dressing surface area in an open, unfurled, or unfolded condition. Alternatively, dressings described herein may provide a small dressing surface are in a closed, furled, or folded condition. The ability of the dressings to be folded, furled, or closed allows them to be more compact and protected for delivery and reduces the likelihood that the dressing surface is prematurely wetted prior to delivery to a target tissue treatment site.

In a preferred embodiment, the dressing is about 50 microns thick, is about 2.5 cm in diameter, and will have an open, unfurled, or unfolded outward facing surface area of about 9.856 cm$^2$. Inside the delivery device sheath (wall thickness of a typical fluorinated ethylene propylene (FEP) delivery tube is about 150 microns), a closed, furled, or folded dressing will have an outward-facing cylindrical surface area (in a 1.25 cm long cylinder) of about 2.07 cm$^2$ inside a 0.45 cm diameter gastroscope channel, or about 1.56 cm$^2$ inside a 0.32 cm diameter gastroscope channel; or about 1.41 cm$^2$ inside a 0.28 cm diameter gastroscope channel. Thus, in one example, a dressing of the present invention may, in an open, unfurled, or unfolded condition, have an outward facing surface area that is about six (6) times greater, about five (5) times greater, or about four (4) times greater than the outward facing surface area of that same dressing when it is in a closed, furled, or folded condition. In some embodiments, the ratio of the outward facing surface area of an open, unfurled, or unfolded to a closed, furled, or folded dressing is about 15:1, or about 14:1, or about 13:1, or about 12:1, or about 11:1, or about 10:1, or about 9:1, or about 8:1, or about 7:1, or about 6:1, or about 5:1, or about 4:1, or about 3:1, or about 2:1.

It is noted that the most common gastroscope channel is 0.28 cm diameter (2.8 mm) and hence this is the most preferred size for the dressing delivery. Alternatively, a more preferred size is 0.32 cm diameter, which is a standard gastroscope channel diameter but less common than the 0.28 cm channel. Another preferred gastroscope channel diameter size is between 0.45 cm and 0.32 cm which is more a custom gastroscope channel size and, thus, less common than the 0.32 or the 0.28 cm gastroscope channel diameter size.

It is able to be folded and unfolded, is not readily soluble in blood or body fluid at about 37° C. within, preferably, the first 6 hours of application, more preferably the first 12 hours of application, and most preferably the first 24 hours of application, and degrades and/or dissolves fully in contact with gastrointestinal fluids at about 37° C. within about 7 days.

It will not adhere to the delivery device, and does not swell or shrink appreciably, i.e., it does not increase or decrease in size by more than about 25% in length and width, or more than about 50% in thickness, in the presence of blood and GI fluid at about 37° C.

In a preferred embodiment, the dressing may be terminally sterilized without affecting dressing characteristics. When it is stored under controlled conditions in its packaging at room temperature of about 21° C. to about 25° C., its tissue adhesion properties, mechanical properties, dissolution properties in gastrointestinal fluid, swelling properties, and hemostatic properties are stable and do not change appreciably over time (e.g., about $\leq$2 years).

A preferred embodiment, the dressing has a tissue adhesive side and a non-adhesive side. In this embodiment, the non-adhesive side may provide a surface that when wet readily slides away from itself and from any applicator or delivery device surface that is applying pressure against the dressing inside a lumen, and/or in the gastrointestinal tract.

A preferred embodiment of the dressing is that it is formed of a substantially dry chitosan composition with a water content of about ≤15%, or about ≤8%. The dry chitosan composition is preferably formed using phase separation and drying of an aqueous solution of chitosan and water. The dry chitosan dressing is preferably prepared in sheet form which may be cut to size.

Preferred embodiments of the biocompatible, bio-dissolvable, tissue adherent chitosan dressing are able to resist dissolution in gastrointestinal (GI) fluid and blood at about 37° C. for at least about 6 hours is tissue adherent and includes materials and material structures that promote resistance to rapid dissolution and degradation in the low pH and strongly enzymatic digestive fluid of the upper gastrointestinal tract. This is a significant advantage of the chitosan dressings disclosed herein because the upper gastrointestinal digestive tract has evolved to rapidly digest most organic materials including chitosan, cellulose and starch.

Chitosan dressings provided herein can be applied to a mucus surface, e.g., in gastrointestinal tract by light pressure. Light pressure applied to the dressing on a tissue surface as used herein indicates a pressure that attaches and keeps a chitosan dressing in contact with an injury site without significant deflection or movement of the tissue so as to allow the chitosan dressing, through its compositional structures and characteristics, to interact to promote adherence with the injury site to stop bleeding. In some embodiments, a light pressure is a pressure at about most preferably 10 kPa or less, more preferably 25 kPa or less, or preferably 50 kPa or less (note 100 g/cm2=9.8 kPa). Typically there is significant deflection on application of load above 100 kPa to soft tissue such as the stomach making application of pressure without a supportive opposite pressure impossible. An exploration of the elastic modulus of the human stomach is provided in Saraf et al. 2007. Saraf, H. et al., *Mechanical properties of soft human tissues under dynamic loading*, J. OF BIOMECHANICS, 40(9), pp. 1960-1967 (2007).

Production of Chitosan Dressing

The chitosan dressings of the present invention may be generated using various methods and processes. In some embodiments, the chitosan dressing may be formed by freeze phase separation and drying. In an alternate embodiment, the dressing is formed by addition of a foaming agent to provide a low density foam before freezing followed by drying. Freeze phase separation followed by removal of frozen solvent by sublimation is called freeze drying. Freeze phase separation is a process of solidification from dilute solution whereby removal of heat and resultant lowering of temperature through a container or mold surface holding the dilute solution results in a localized solid crystal nucleation of pure solvent and subsequent propagation and growth of pure solvent crystal. A result of the pure solvent crystal growth in a dilute solution is that solute diffuses away from the growing crystal front to solidify at the interstices between the growing crystal. Freeze phase separation of dilute polymer aqueous solutions results in alternate layers of thin polymer lamella between thicker layers of ice. Removal of the ice by methods which do not disrupt the polymer lamella results in a low-density polymer dressing with inter-connected porous structure. For example, in one embodiment, low-density polymer dressings may have an initial dressing density from about 0.005 g/cm³ to about 0.05 g/cm³.

In an alternate embodiment, the freeze phase separated dressing is formed by freezing of a foamed dilute solution followed by drying. In an alternate embodiment, the dressing is formed by non-woven fiber spinning processes, such as centrifugal spinning, electrospinning or solvent fiber extrusion into a coagulation bath. In yet another alternate embodiment, the dry dressing of the invention may be formed from a woven fiber process. In yet another alternate embodiment, the dry dressing of the invention may be formed by phase inversion and precipitation with a non-solvent (as is typically used to produce dialysis and filter membranes). In still another alternate embodiment, the dressing of the invention may be formed from an additive 3D printing process.

In a preferred embodiment of the invention, the dressing preparation process may include a compression process that changes the initial dressing density from an initial preferred range of about 0.005 g/cm³ to about 0.05 g/cm³ to a final preferred range of about 0.03 g/cm³ to about 0.7 g/cm³; however, ranges of about 0.08 g/cm³ to about 1.2 g/cm³ are also contemplated. It is noted that a density of about 1.5 g/cm3 is the density of void-free chitosan dressings. The compression process may include application of temperature in the range of about 20° C. to about 150° C. To avoid substantial dressing swelling of the dry compressed dressing on contact with biological fluid, the temperature of the compression is preferably applied by a method that may include but not be limited to convection, conduction and radiation, and the temperature of the compressed dressing should preferably be maintained at least about 80° C. for at least about 15 seconds.

Heat during compression is a tool that allows plasticization and molding of the chitosan without cracking or tearing of the chitosan (non-destructive molding). The first glass transition temperature (Tg) of pure dry chitosan is near 80° C. which if processed near in the case of pure dry chitosan will allow ready non-destructive molding of the chitosan as well as some crystalline annealing of its structure. It is possible to lower the Tg by application of plasticizers such as water or glycerol to the chitosan and hence provide a similar level of non-destructive molding at lower temperature. Here, it is noted that chitosan can be molded non-destructively in the range 20° C. to 150° C. Outside of this range it would still be possible to non-destructively mold the chitosan but much more difficult. Above 150° C. the chitosan begins to thermally degrade while below 20° C., the addition of plasticizers may lead to undesirable loss of chitosan crystallinity which provides for dissolution resistance and resistance to degradative processes such as occur in sterilization.

Preferably, the compression prevents substantial swelling of the dry compressed dressing on contact with biological fluid and is performed with moisture content of the dry dressing during the compression at about ≤15% w/w. The compression may be applied through twin or multi-roller compression and/or uniaxially between adjacent platens.

The compression may be against a uniform flat or curved surface to provide a smooth finish to the compressed dressing.

Alternatively, the compression may be applied against an etched, machined, ablated or other type of surface treatment that imparts a depleted or added surface texture. The surface texture may be a random or it may be a regular repeated pattern. The pattern of the surface may assist in folding and unfolding or furling and unfurling the dressing and may provide for hinge-like properties in the dressing. Such texture may be used as an adjunct to quickly lock the dressing in place and stop it moving when applied. Movement of the surface of the dressing while positioned against the target tissue surface can cause filming and hence closure of the open surface structure which can lead to loss ability to remove anti-adhesive biological fluid at the surface and hence loss of ability to adhere the dressing to the surface. The timescale of the changes occurring at the dressing surface is very important such that surface uptake of fluid with significant surface dressing channel closure is highly undesirable. A good way to avoid such movement is to physically fix the dressing in place as soon as it contacts the tissue surface.

Prior to the present invention, thin solid chitosan dressings were generally rigid, not flexible enough to be bent or folded or furled without breaking, fracturing, or otherwise losing their intact shape or becoming otherwise unsuitable for use. Chitosan dressings provided herein, due to their compositional structures and characteristics, can be folded and unfolded along a folding axis while still being intact and suitable for use in stopping bleeding. Interestingly, and contrary to expectation, it has been found that chitosan dressings described herein, when folded, become less resistant to tearing or breakage along their folded seams. In some embodiments, the chitosan dressing provided herein, due to its compositional structures and characteristics, can be furled without losing its compositional structures and characteristics and still being intact and able to stop bleeding. In some embodiments, the chitosan dressing provided herein, therefore, is able to be delivered through a narrow working channel while still maintaining their compositional structures and characteristics intact. Exemplary diameters of a narrow working channel through which the chitosan dressing provided herein can be delivered include a diameter of about 3.2 mm or less, and including, but not limited to, 0.1 mm, 0.2 mm, 0.3 mm, 0.4 mm, 0.5 mm, 0.6 mm, 0.7 mm, 0.8 mm, 0.9 mm, 1.0 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm, 3.1 mm, and 3.2 mm.

Catechol Modified Chitosan; and Its Production

The chitosan dressings described herein relate to chitosan dressings comprising catechol modified chitosan and/or hydrophilic polymers. Other aspects of chitosan dressing comprising catechol modified chitosan are described in more details below.

Preferred embodiments of the chitosan gastrointestinal dressing of the invention include compositions with catechol modified chitosan and/or, optionally, other hydrophilic polymers. Preferably the catechol modified chitosan in the dressing provides prolonged adherence to wetted tissue with tissue adherence ≥ about 1 kPa resisting dissolution in water, saline solution, blood and/or GI fluid at about 37° C. for ≥ about 6 hours. Preferably the catechol modified chitosan is formed by N-acylation of the C-2 amine on the chitosan glucosamine by 3,4-dihydroxyhydrocinnamic acid (alternatively named 3-(3,4-Dihydroxyphenyl)propionic acid, Hydrocaffeic acid)). Alternatively, the chitosan N-acylation to produce a catechol modified chitosan may include but not be limited to a modification with one of a 3,4-Dihydroxycinnamic acid (caffeic acid); a trans-3,4-Dihydroxycinnamic acid (trans-caffeic acid); and a 3,4-Dihydroxyphenylacetic acid (DOPAC, Homoprotocatechuic acid).

The presence of catechol in the composition provides for some poly-conjugated structure as the catechol is oxidized to o-quinone. This causes visible difference between the unmodified chitosan and catechol modified chitosan compositions, which may be off-white or pink to dark brown in color, respectively. It is noted that the catechol modified chitosan compositions go from pink to brown when oxidation occurs in the catechol.

Pink coloration in the catechol modified chitosan, signifying substantial absence of crosslinking, is provided in the aqueous synthesis by maintaining pH reaction solution at or below pH 5.5. The pink coloration may also be provided in the aqueous synthesis by performing the modification and subsequent processing steps substantially in the absence of oxygen such as by using aqueous systems purged with an inert gas which may include but not be limited to argon or nitrogen. Although the pink coloration is not desirable in the final solution or catechol modified product, it may be desirable in intermediate handling stages (such as immediately after chitosan derivatization with catechol and/or dialysis and/or washing of the subsequent catechol chitosan solution to remove residual unreacted material) because it allows for stable dry product polymer storage and dry product weight determination with subsequent ability to substantially re-dissolve the pure dry catechol modified product in water to a desired dry weight at a later time. This water-soluble chitosan catechol material is then subsequently oxidized and crosslinked (with brown coloration). However catechol modified chitosan which is dried before oxidation is not suitable for use in the chitosan dressing of the invention because dressings including such treated catechol modified chitosan are not readily redissolved and the final solution includes an undesirable mass fraction (>5% w/w) of insoluble particulate (>10 microns in diameter). Additionally catechol chitosan prepared after an intermediate freeze drying stage is more prone to early dissolution in gastrointestinal fluid.

In a preferred embodiment, the catechol modified chitosan is not removed from solution by an intermediate drying step to allow for storage but rather it is kept in aqueous solution and oxidized in aqueous solution by exposure to higher than about pH 5.5 in the presence of atmospheric oxygen. Preferred pH control is achieved by adjustment of partial pressure of aqueous dissolved carbon dioxide (increased partial pressure reduces pH while decreased partial pressure increases pH to nearer pH 7). An alternative preferred means of pH control is by incremental addition of a strong acid to lower pH and a strong base to raise pH. Examples of strong acids may include, but are not limited to, hydrochloric acid, sulphuric acid and nitric acid. Examples of strong bases may include but not be limited to sodium hydroxide and potassium hydroxide. Subsequent drying of this aqueous water-soluble oxidized catechol modified chitosan results in a preferred level of crosslinking of the catechol chitosan with good resistance to dissolution and degradation in the upper gastrointestinal tract. The catechol chitosan solution may be diluted by addition of water or concentrated by water removal. The water may be removed by the techniques including, but not limited to, ultrafiltration, reverse dialysis and centrifugation. The solid fraction of the solution may be determined by sampling a known volume from the solution and performing analyses including but not limited to gravimetry, fourier transform infrared spectroscopy, ultraviolet-visible spectroscopy, refractometry, and pycnometry.

Figure 5:
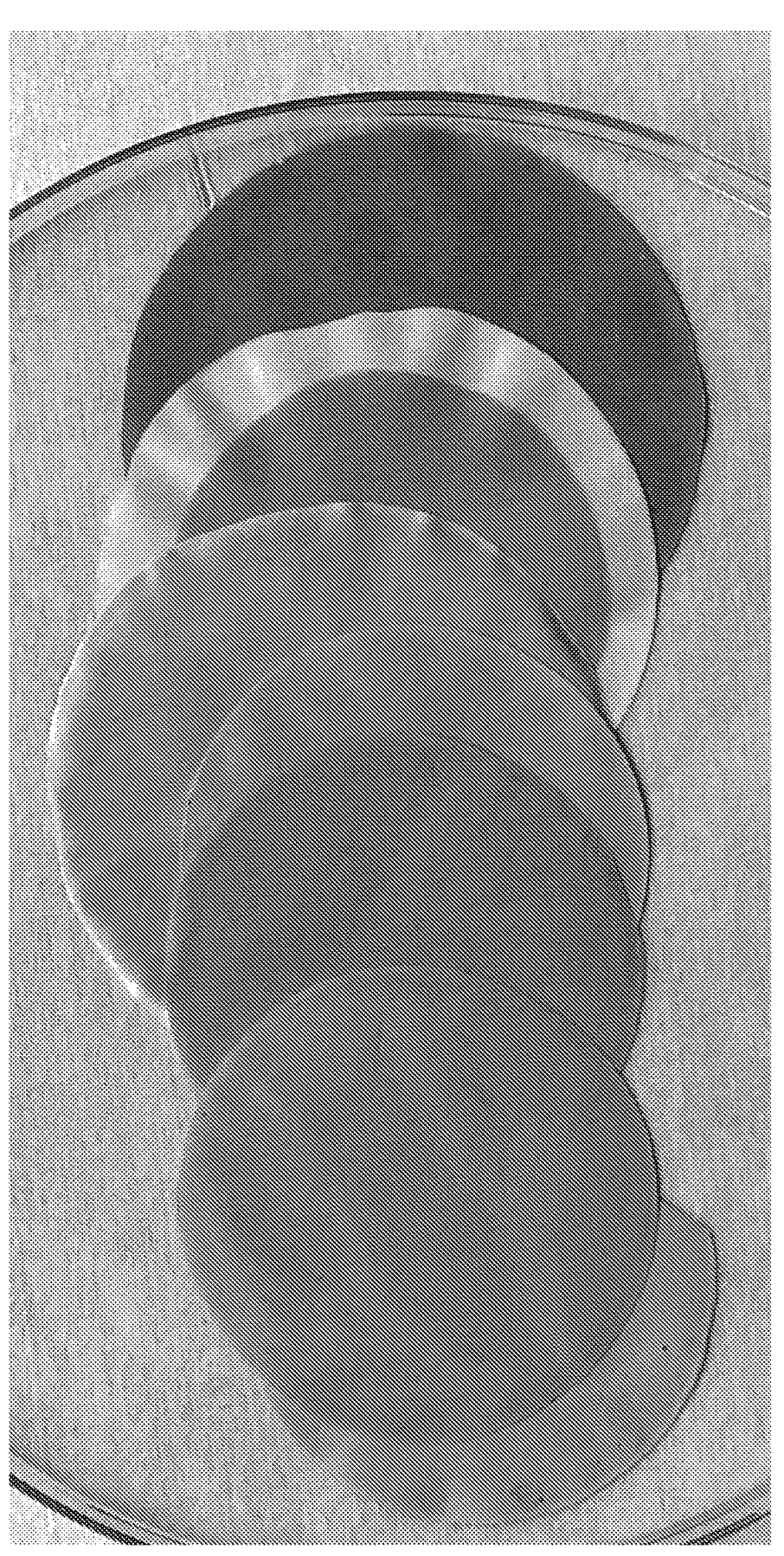
FIG. 5 depicts round-shaped catechol modified chitosan dressing that are (pre-cut) 2.5 inch & 2 inch diameter compressed to near 50 microns. The coloration of these catechol modified chitosan dressing, starting from left to right, ranges from light pinkish brown (first dressing), 2 dressings of darker pinkish brown, 2 tan brown colored dressings (no pink), 1 brown dressing and lastly 1 darker brown. Catechol chitosan dressings 5 & 6 are formed from 2.5" and 2" molds and they are backed with unmodified chitosan dressings both from 2.5" molds and the unmodified chitosan can be seen clearly as the white halo (no brown or pink color) in dressing 6. The catechol chitosan and unmodified chitosan dressings were adhered together during compression to a final shared density >0.4 g/cm3. The pink coloration is associated with unoxidized catechol while the brown color is associated with the oxidized catechol (o-quinone). The lighter browns and lighter pinks are associated with lower degree of substitution of the chitosan with catechol (nearer 10%) while the darker colorations (pinkish brown & brown) are associated with higher degree of substitution of the chitosan with catechol (nearer to 20%).

In a preferred embodiment, the catechol modified chitosan composition is of a brown color resulting from catechol oxidation to o-quinone. The quinone is produced by autoxidation of the catechol hydroxyls in the presence of oxygen and at pH above about 5.5. Schiff base reaction of quinone with chitosan C-2 amine produces crosslinking in the modified chitosan. The color of the catechol modified chitosan composition is controlled during synthesis by controlling pH and oxygen exposure. Maintenance of pH at or below about pH 5.5 inhibits the production of o-quinones. Subsequent conditioning of dialysis solution, final washed, or dialysed catechol chitosan solutions in a preferred pH range 5.8 to 6.2 provides for more dissolution resistant, darker, more oxidized catechol. In some embodiments, the coloration of catechol modified chitosan characterizes one aspect of the catechol modified chitosan dressing. In some embodiments, the coloration reflects the degree of substitution of the chitosan with catechol. In some embodiments, the coloration from pink to brown correlates with the degree of substitution. FIG. 5 shows exemplary embodiments of different colorations reflecting and correlating with different degree of substitution of the chitosan with catechol.

In order to prepare a dry dressing from the catechol chitosan, a preferred light brown to darker brown catechol aqueous chitosan solution is prepared which may be used by itself or may be mixed with other aqueous hydrophilic polymer solutions including but not limited to solutions of chitosan and/or, optionally, hydrophilic polymers. Preferably, the dry phase separated catechol chitosan dressings are prepared as densified dried freeze-phase-separated and fibrous dressing structures.

Preferred crosslinked catechol modified chitosan compositions of the invention provide good tissue adherence and 10 times to 100 times increased resistance to dissolution in the upper gastrointestinal tract compared to dressings formed substantially of unmodified chitosan. For example, FIGS. 6A-6C show dissolution testing results demonstrating that chitosan dressings are gone in 15 minutes while some catechol dressings lasted greater than 24 hours. The catechol modified chitosan compositions described herein, provide hitherto unknown longevity, biocompatibility, and ability to eventually dissolve.

Preferred rapid adherence to gastrointestinal mucosa of the chitosan gastrointestinal dressings of the invention ($\leq 1$ minute) is provided in the dry chitosan dressing by the promotion of quaternary ammonium cation formation at the chitosan glucosamine C-2 amine by the presence of an acid in the dry dressing composition. Preferred chitosan acid salts in the dressing may include salts of acetic, lactic, glycolic, citric, succinic, malic, hydrochloric, glutamic, ascorbic, malonic, glutaric, adipic, pimelic, and tartaric acids, and combinations thereof. Preferably the acid salt % weight of the chitosan is greater than about 2% and less than about 15%. To achieve fast adherence (e.g., $\leq 1$ minute) to wet tissue, the moisture in the dry gastrointestinal dressing is preferably less than about 15% by weight; more preferably it is less than about 10% by weight and most preferably it is less than about 5% by weight.

In the case of densified freeze-phase-separated and dried chitosan dressings, the chitosan solution is poured into the freeze-phase-separation mold (typically in the shape of a pan with a horizontal flat base) with preferably around a 0.1% w/w, more preferably around 0.5% w/w and most preferably 0.25% w/w hydrophilic polymer chitosan solution. The hydrophilic polymer solution is preferably added to the horizontal flat pan to a vertical depth of preferably about 10 mm, more preferably 2.5 mm and most preferably 5.0 mm mold depth. The solution in the mold is subsequently frozen and dried to remove water by sublimation or freeze phase substitution (solvent extraction of the ice with a non-solvent to the polymer) to a low density (>99% void volume) open or porous dry sponge with a dry density < about 0.01 g/cm³ (or, for example, about 0.005 g/cm³ for a catechol chitosan uncompressed dressing from 0.5% solution, which is about ⅕ or 20% of the density of an uncompressed HemCon Bandage chitosan sponge, which is about 0.025 g/cm³). Lyophilization is typically performed at pressure below 300 mTorr while freeze substitution involving a dry, cold (e.g., <−20° C.) solvent such as ethanol is performed at atmospheric pressure. The dry sponges are then compressed, preferably to greater than about 0.4 g/cm³ density and less than about 100 microns thickness. The preferred compression is not limited to but may include uni-axial compression between aligned flat platens, wherein the platens are heated between 18° C. and 150° C. and are pressure loading up to 10,000 bar.

The preferred compression creates a remarkably thin (e.g., range from about $\leq 50$ microns to about $\leq 200$ microns) strong (e.g., 5 MPa to 25 MPa UTS) readily foldable chitosan dressing that may be placed minimally invasively anywhere in the body in a confined folded form that can be reformed without compromised performance to the original unfolded dressing form for accurate and effective high surface area placement and attachment.

Figure 7:
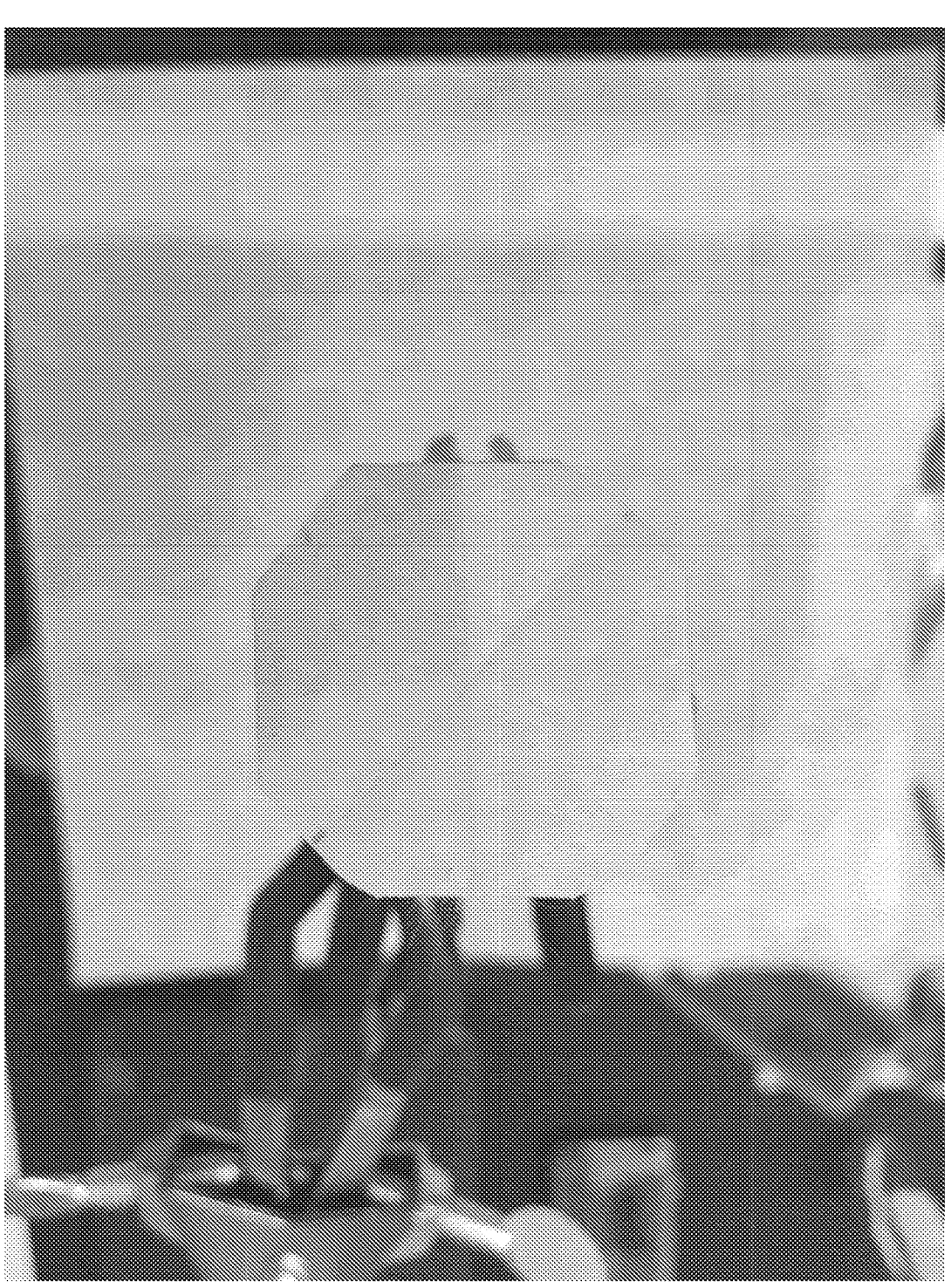
FIG. 7 depicts a catechol modified chitosan dressing that has been folded and unfolded, remaining intact with visible fold axis (crease).
Figure 9:
FIG. 9 depicts a gastroscope digital image of the modified catechol chitosan dressing of the invention intimately adhered to stomach mucosa, demonstrating slight swelling in the stomach environment, and effectively controlling upper gastrointestinal hemorrhage (Forrest 1a) of a lacerated gastroepiploic artery inside the stomach of a heparinized swine 3 hours after application of the dressing to the arterial injury.
Figure 10:
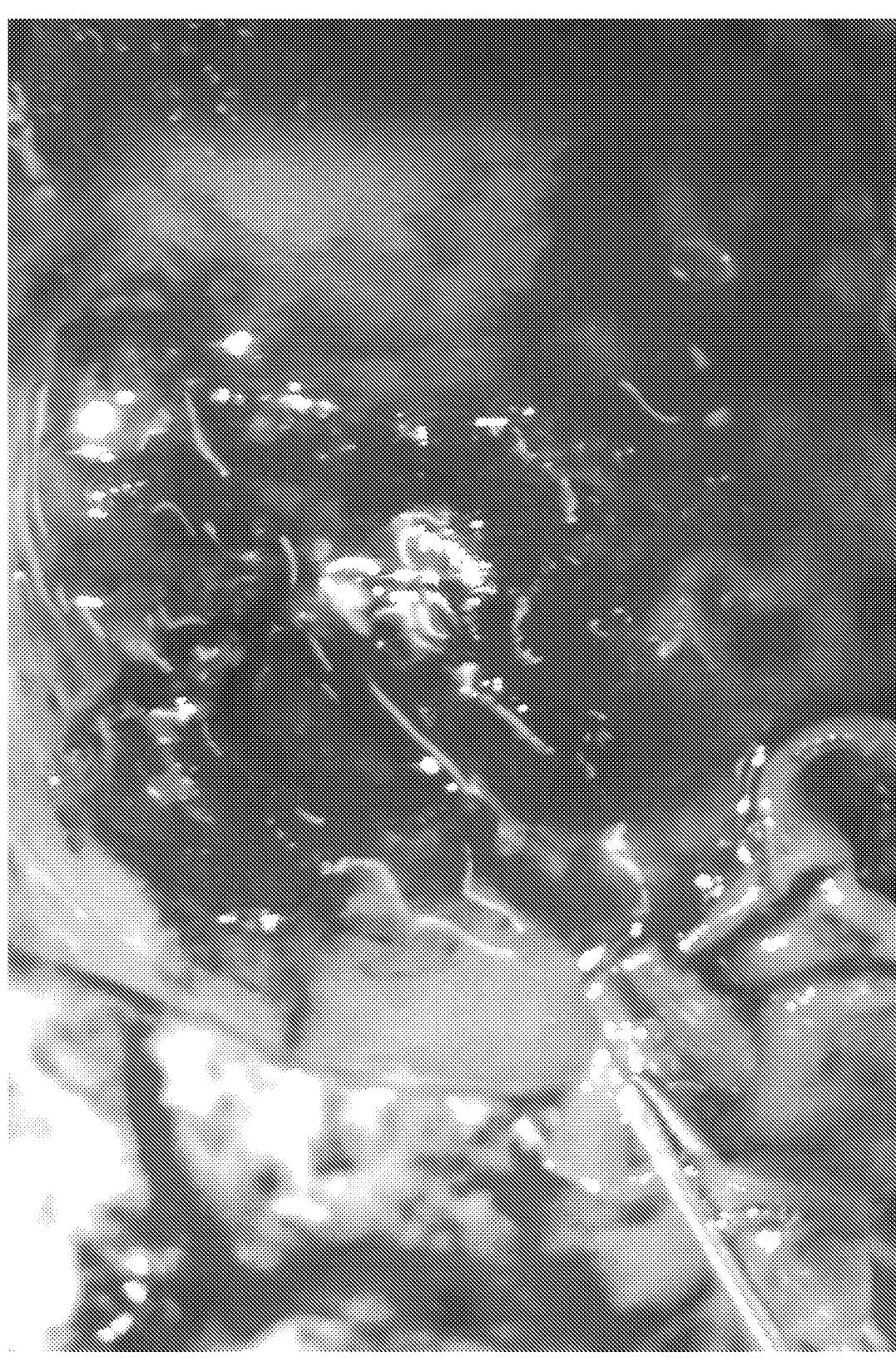
FIG. 10 demonstrates the presence of a strong intact clot under the dressing of FIG. 9 at animal sacrifice which was within 45 minutes of taking the image of FIG. 9. The modified chitosan dressing was shown to be uniformly adhered to the injury and stomach mucosa at sacrifice.

Foldability is addressed in the examples below. In one embodiment, fold testing involved folding the horizontally planar final compressed circular dressing through 180° edge over edge, first in an anticlockwise direction, holding the edges together and compressing firmly in the middle of the dressing to create a single linear fold axis (or crease) in the dressing. The folded dressing is then opened and the edge to edge fold is reproduced in the new fold axis but with the folding in the opposite clockwise direction. Foldability success can be rated as no tears or cracks being visible along the fold axis and no significant loss in tensile properties of the dressing (determined by gentle pulling across the fold of the dressing). FIG. 7 shows a catechol modified chitosan dressing that has been folded and unfolded, remaining intact, with visible fold axis (crease).

Freeze phase separation of dilute aqueous polymeric solutions results in phase separation of micron and submicron thin polymeric chitosan lamella interspersed regularly between ice crystal sheets close to 200 microns in width. Removal of the ice by sublimation (freeze drying) or alternatively by solvent extraction leaves the dry sponge composed of close-to-aligned, thin ($\leq 1$ micron), polymeric chitosan lamella. Compression of the polymeric chitosan lamella at close to or greater than their glass transition temperature (Tg for dry chitosan is near 80° C.) allows for their compression into the thin (near 50 microns) dense polymeric structure formed of layers of hundreds of strong compliant polymeric chitosan leaves (lamella) which do not readily propagate cracks and which can be folded repeatably without failure. Such multi-leaf layering achieves remarkable strength. Prior to the present invention, no one has previously investigated high-density freeze-phase-separated chitosan dressings for manufacture and use as described herein and with the aim to address key problems solved by the present invention such as, for example, adhesion by removal of interfering fluids (by absorption, channeling, displacement, and/or re-direction), ability to form a fold axis and ability to resist mechanical failure on repeated folding and unfolding along the fold axis.

In one embodiment, porosity (void space >99%) is complete and uninterrupted in the non-compressed dressing with pore size range of 20-300 microns with substantially most of the pores near 100-200 microns. The un-interrupted pore structure is indicated in the compressed dressings by their ability to absorb biological fluid such as blood.

In some embodiments, crack free, clean edge holes near 500 microns in diameter may be formed in the dressing after compression by localized application of narrow gauge (near 500 microns in diameter), sharp pointed needle through the dressing and into a flat, hard elastomeric surface applied immediately against the dressing which may receive and release the point of the needle. Preferred receiving support flat surfaces include but are not limited to clean, dry thermoplastic elastomers with Shore 55D to 90D in hardness. Alternative methods of hole formation may include but not be limited to use of a small diameter (near 500 microns) hole punch or a laser cut hole.

In com embodiments, chitosan dressing provided herein has holes in the dressing. In some embodiments, the holes receive fiber or other reinforcing attachment elements. Such reinforcing element may be formed by simple local application of a reinforcing fluid to locally bind with the edges of the holes. A reinforcing fluid used in the development of the present invention included cyanoacrylate glue which bound the compressed chitosan lamella of the dressing together and prevented local delamination and fibrillation of the chitosan at the hole stress point. Another embodiment of a hole reinforcing element is micro-molded interlocking parts of plastic or metal (dissolvable in the upper gastrointestinal tract or alternate area in the body of application) that are placed on one side of the hole and the opposite hole side to permanently fit together and be able to support load through the hole without causing dressing delamination, fibrillation or other stress related failure at the dressing hole when loaded. In some embodiments, the micro molded parts may include the part on the side of the attachment to a delivery device that enables convenient snap-on attachment and snap-off detachment of the dressing to the delivery device.

As used herein, the term fold axis is intended as part of the dressing sheet which demonstrates memory in the material of bending stress and or folding and is typically localized to narrow regions of high bending stress and shear. A crease in folded paper is an example of a fold axis.

In a preferred embodiment, the tissue adhesive component of the dressing is formed from a freeze phase separated and dried chitosan sheet with composition including a catechol chitosan. In a preferred embodiment the non-tissue adhesive component of the dressing is formed from a freeze phase separated chitosan dried sheet without any modified chitosan. In a preferred embodiment, both tissue adhesive and non-tissue adhesive dry sheets have density ≤ about 0.03 g/cm³ before compression to final density ≥ about 0.4 g/cm³.

In order to prepare one dressing from both sheets with the dressing having a tissue adhesive surface layer and a non-adhesive surface layer, the two sheets are bonded together by, for example, placing one sheet on top of the other and applying sufficient uniform pressure over the dressings to compress them to a higher density. In a preferred process, the original densities of each sheet type at ≤ about 0.03 g/cm³ is increased to a final dressing density ≥ about 0.30 g/cm³. In a more preferred process, the original densities of each sheet type at ≤ about 0.015 g/cm³ is increased to a final dressing density ≥ about 0.4 g/cm³. In a most preferred process, the original densities of each sheet type at ≤ about 0.01 g/cm³ is increased to a final dressing density ≥ about 0.5 g/cm³. At the conclusion of the compression, the two compressed sheets are bonded together so that one cannot be readily peeled away from the other and the dressing can be manipulated by folding and furling without any occurrence of separation.

This physical adherence of materials by compression of two or more low density porous materials together to form a final two or more layer porous material of higher density solves a difficult problem of how to adhere such materials together without physical or chemical change to the individual materials and without addition of further bonding agents or adherents. It is contemplated that bonding may be attributed to microsurface impingement and penetration of the dressings through their pores with physical interlocking due to pore compression. This physical interlocking of low density, freeze phase separated, dry sheets is not restricted to two materials of the same thickness or to only two layers since the interlocking effect is neither sidedness nor thickness dependent. Therefore a multi-layered construct of individual freeze phase separated and dried sheets of the same or different materials of the same or different thickness may be formed by layering the low density sheets (preferably with density ≤0.05 g/cm³) and compressing the assembly together to a density ≥0.3 g/cm3). Such a final physically adhered assembly would be expected to provide advantages of thin top and bottom surface layers including but not limited to adhering or anti-adhering materials with layers inside providing including but not limited to structural, physical and chemical elements.

In some embodiments, a chitosan dressing has an adhesive side and a non-adhesive side. In some embodiments, the adhesive side of the chitosan adheres to a tissue and absorbs and/or redirects the surface moisture. In some embodiments, the non-adhesive side detaches from a delivery device upon attachment of the chitosan dressing to the injury site wherein the chitosan dressing has become wet. This is in part because the adhesion strength of the chitosan dressing to the tissue surface controls the dressing location upon detachment of the dressing from the delivery device. Detach or "readily detach" as used herein in a two-sided chitosan dressing indicates that the chitosan dressing, with its adherent side applied to a tissue surface or an injury site and adhered due to absorbance of moisture, stays at the tissue surface or injury site while the non-adherent side releases from the delivery device, thereby allowing the delivery device to be retracted from the injury site without disrupting the position of the chitosan dressing on the tissue surface or injury site. In some embodiments, the chitosan dressing, when dry, attaches to the delivery device, thereby allowing delivery of the chitosan dressing along with the device onto an injury site.

In one embodiment, there is a need to attach the dressing locally to the delivery device. Generally, these local attachment areas are at the extremity of the dressing. For example, one design is to provide for local pinpoint attachment on the dressing extremity tabs at the circumference of the dressing and for no other attachment locations to avoid the risk of attaching the dressing to the delivery sheath, the delivery device, or itself (when furled/folded). The attachment locations may be designed to weaken when wet or alternatively be activated for release by some type of physical release mechanism.

In one mechanism, chitosan dressing provided in this disclosure is able to stop bleeding by absorbing, channeling, and/or redirecting the hydrophilic and hydrophobic fluids at an injury site. The absorption clears enough moisture from the injury site to allow subsequent hemostatic reactions between the chitosan dressing and the tissue at the injury site, which in turn stops bleeding and allows the chitosan dressing to stay attached; thus, sealing the injury site. The porous, dense, and multi-layer structure of chitosan dressing provided herein facilitates the absorption, channeling, and/or redirection of the moisture at the injury site, and the attachment or adherence of the chitosan dressing to the injury site.

The chitosan dressing disclosed herein is biocompatible. In some embodiments, the dissolved residue from a chitosan dressing applied to an injury site in vivo passes safely through the alimentary tract and is excreted along with other bodily waste.

More than one, or multiple, chitosan dressings may be used or applied in serial fashion to a tissue treatment site or injury site. When more than one chitosan dressing is deployed, such dressings may separately adhere to adjacent tissue site or injury site areas, or may overlap with each other to varying extents. Due to the thinness of the chitosan dressing described herein, depending on the application, it is contemplated that multiple chitosan dressings may be used as needed to promote or achieve hemostasis of an injury site.

In one embodiment, the chitosan dressings overlap one another upon application. In such an instance, ideally there would be some adherence of the wetted adhesive side of the subsequent dressing to the wetted dressing backing of the earlier dressing. Accordingly, in one embodiment, the chitosan dressing does not have an anti-adherent backing but does have a backing with a weak wet adherence that provides for sufficient adherence for placement of a subsequent overlapping chitosan dressing.

Delivery Device

A delivery device, as used herein, is a device for delivering chitosan dressing. A delivery device delivers a chitosan dressing to injury sites at different locations in the body of an animal including human, pigs, dogs, etc.

In some embodiments, a delivery device is a minimally invasive device that can deliver a therapeutic, e.g., a chitosan dressing, to a physiological site in the body of an animal, in non-invasive or minimally invasive manner. In some embodiments, the delivery device is a balloon device. In some embodiments, the delivery device is a wire device or a device laser-cut from a small diameter cylinder of nitinol or stainless steel. In some embodiments, the non-invasive or minimally invasive feature of the delivery device is achieved through delivery of a therapeutic, e.g., a chitosan dressing, through a narrow catheter or a comparable working channel. In some embodiments, the catheter or the comparable working channel has a diameter that is less than 3.2 mm. In other embodiments, a gastroscope channel may range in diameter size from 2.8 mm to 4.5 mm.

Exemplary delivery devices include, but not limited to, a balloon device, a balloon catheter, a wire device, a cylindrical device with laser-cut ends, a indwelling catheter, a urethral or suprapubic catheter, an external catheter, a short-term catheter, and an intermittent catheter.

A delivery device can also be an endoscopic device used in various aspects of medical procedures. In some embodiments, the endoscopic device is non-invasive or minimally invasive due to a narrow catheter or tube/tubing or a similarly narrow-diameter portion of the device.

Delivery devices include other devices with narrow-diameter tubings or catheters or similar structures.

Attachment of the Dressing to the Delivery Device Freeze phase separated dressings are composed of compacted layers of friable and delamination prone lamella that require special attachment of the dressing to wire and cylindrical laser-cut delivery devices. Each dressing attachment point to the delivery device must be able to withstand up to 50 to 100 g of load during furling and unfurling of the dressing. Because of the low cohesion strength of surface lamella, direct adhesion (such as by cyanoacrylate glue) of the dressing to the delivery device is not an option for freeze phase separated dressings formed from well dissolved solutions. One embodiment where this is less problematic is where the catechol chitosan is formed from carbonic acid dissolved chitosan wherein the base precipitated and subsequently water-washed pure chitosan aqueous gel before dissolution in the carbonic chitosan contains a dispersion of solid chitosan fibers ($\geq$0.2% w/w of the chitosan) insoluble in the carbonic acid that provide reinforcement to the subsequently catechol modified chitosan from carbonic solution. Besides this carbonic acid chitosan instance of a low fraction (0.2% to 5% w/w of the chitosan) chitosan fiber reinforcement of the freeze phase separated bulk and surface structure of the dressing, the preferred manner of local reinforcement and attachment of the dressing to the delivery device in the case of wire delivery is by placement of small diameter (near 500 microns), through and through holes with reinforcement elements in the dressing at the points of attachment to the delivery device.

Preformed holes in the freeze phase separated, dried dressing sponge are a preferred way to make receiving holes in the uncompressed dressing sponge. Because the low density uncompressed sponges (<0.05 g/cm3) readily delaminate, are highly friable and thus cannot receive normal hole making approaches which involve any load on the sponge, the preferred method to make holes in these sponges without any damage to the sponge lamella structure is to apply insulating, hydrophobic (non-adherent) rod mandrels to the mold solution (from the top of the solution, through the solution to the other side and contacting the base surface of the mold and preferably through the base surface and into the base of the mold) immediately before freeze phase separation of the solution. These mandrels may be tapered to allow ease of removal after drying of the freeze phase separated sponge. It is envisioned that such mandrels would be made of a rigid or semi-rigid hydrophobic material that could be machined or molded. Mandrel materials that would be suitable include but are not limited to the fluorinated materials Teflon™ and Kel-F™ and high density polyethylene (HDPE). The diameter of the hole made after removal of the mandrel is designed to allow thread to be easily placed through friable uncompressed sponge without damage to the sponge. The mandrels may be supported in the mold by slotting into suitably sized receiving holes in the mold base surface. Alternately they may be supported by a sheet of releasable hydrophobic film placed immediately over the upper surface of freeze phase separation mold and the mold solution. This film would be removed from the frozen phase separated surface, leaving the mandrels in place, before drying in the case of drying of the freeze phase separated solution. After drying, the preformed holes are thus ready to receive tie thread for attachment of dressing to delivery/deployment device. The tie thread is positioned in sponge before compression in suitable arrangement to take all the forces on dressing furling, unfurling, and delivery. Compression of sponge (from low density <0.05 g/cm3) to high density (>0.4 g/cm3) locks the tie thread and any other element of reinforcement/attachment in place. The thread may be glued in place before or after dressing compression or the thread may be used to locally apply a liquid reinforcing element such as cynanoacrylate glue locally through the hole with the thread removed after application. An alternate embodiment for forming suitable holes in the uncompressed sponge for taking a supporting thread or other type of supporting element is by laser hole cutting.

Crack free, clean edge holes near 500 microns in diameter may be formed in the dressing after compression by localized application of narrow gauge (near 500 microns in diameter), sharp pointed needle through the dressing and into a flat, hard elastomeric surface applied immediately against the dressing which may receive and release the point of the needle. Preferred receiving support flat surfaces include but are not limited to clean, dry thermoplastic elastomers with Shore 55D to 90D in hardness. Alternative methods of hole formation may include but not be limited to use of a small diameter (near 500 microns) hole punch or a laser cut hole.

Holes in the dressing can receive fiber or other reinforcing attachment elements. Such reinforcing element may be formed by simple local application of a reinforcing fluid to locally bind with the edges of the holes. A reinforcing fluid used in the development of the present invention included cyanoacrylate glue which bound the compressed chitosan lamella of the dressing together and prevented local delamination and fibrillation of the chitosan at the hole stress point. Another embodiment of a hole reinforcing element is micro-molded interlocking parts of plastic or metal (dissolvable in the upper gastrointestinal tract or alternate area in the body of application) that are placed on one side of the hole and the opposite hole side to permanently fit together and be able to support load through the hole without causing dressing delamination, fibrillation or other stress related failure at the dressing hole when loaded. It is envisioned that such micro molded parts may include the part on the side of the attachment to the delivery device that enables convenient snap-on attachment and snap-off detachment of the dressing to the delivery device.

General delivery device release of dressing may be achieved by a number of methods include snap-off detachment. A preferred method of dressing release is by using a delivery device to dressing attachment fiber that is strong when dry and weak when wet. Such fiber includes but is not limited to chitosan fiber that has been treated to become rapidly water soluble. Preferred chitosan fiber is water soluble multifilament fiber with strength >30 MPa when dry and < than 0.1 MPa when wet.

Applications and Methods of Treatment

The chitosan dressing provided in this disclosure may be used to stop bleeding in suitable diseases, conditions, disorders, or emergent traumas or injuries. In some embodiments, the dressing may be used to stop bleeding from any wet physiological surface, e.g. mucus. Exemplary applications include, but are not limited to, gastrointestinal tract bleeding, other intraluminal applications, including vascular applications, internal surgical bleeding, internal biopsy bleeding, internal bleeding following parenchymal organ resection, and oral, ocular, auditory or nasal bleeding. Additional applications that might require addition of water or fluid to encourage adhesion of the chitosan dressing to a tissue surface or injury site are also contemplated, for example, use of the chitosan dressing on external body surfaces.

Chitosan dressings of the present invention may be used for treatment of gastrointestinal bleeding that may include but not be limited to treatment of bleeding in esophageal varices, bleeding from peptic ulcers, bleeding from duodenal ulcers, bleeding associated with biopsy of the upper and lower gastrointestinal tracts, resections of the upper and lower gastrointestinal tracts, and tears or ruptures in the upper and lower gastrointestinal tracts. Other diseases, conditions, disorders, or emergent traumas or injuries may include, but are not limited to, internal arterial injury; internal bleeding from the liver, internal bleeding from the vena cava; injury in the thoracic cavity including perforations of the heart and lungs and their vessels; and injuries of the abdominal cavity.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including, but not limited, to U.S. Provisional Patent Application No. 62/611,994, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

EXAMPLES

In the development of the chitosan gastrointestinal hemostatic dressing (CGHD) of the invention different prototype dressing compositions were investigated to prepare foldable, mucoadhesive and cohesive chitosan dressings with sustained hemostatic efficacy at pH close to 4. Such thin high-surface area hemostatic dressings which are uniquely well-suited for use in extreme physiological environments, including (but not limited to) the stomach and other parts of the GI tract, and capable of delivery using minimally invasive techniques due to their small volume relative to strength and treatment surface area capacity, have not been previously described. There is an urgent need for such dressings. The CGHD dressings disclosed herein defied conventional expectations as to what may be expected from, or achieved using, chitosan based materials to form hemostatic, thin, high surface area, low volume, foldable, strong, low pH dissolution resistant, adherent, biocompatible dressings.

CGHD formulations were assessed in vitro for long-term, mechanical resilience, ability to be delivered, low pH/wet adherence, hemostatic ability and ability to be left in place, and to be digested or dissolved in less than 168 hours, or one week (7 days). Prototypes were screened in an acute stomach injury model before down selection to best performing dressings for ≥3 hour application control of non-variceal upper gastrointestinal bleeding (UGIB). In vivo swine models of gastric arterial bleeding were used to assess acute and prolonged (≥3 hours) control of brisk (class 2A) non-variceal UGIB.

The following materials were used in the gastrointestinal chitosan hemostatic dressing development:

Chitosan A: Primex ChitoClear 65010, TM 4375, MW=250-300 kDa, Brookfield viscosity in 1.0% w/w chitosan solution in 1.0% acetic acid at 25° C. and spindle LV1=390 cPs, DDA=80% (by colloidal titration).

Chitosan B: Primex ChitoClear 43000, TM 4167, MW=110-150 kDa, Brookfield viscosity in 1.0% w/w chitosan solution in 1.0% acetic acid at 25° C. and spindle LV1=9 cPs, DDA=95% (by colloidal titration).

Glacial acetic acid: Fisher Scientific, Catalog No. A38-212.

Hydrochloric acid: 1.0 M aqueous solution Sigma Aldrich, Catalog No. H9892.

L-Lactic acid: JT Baker, Catalog No. 0196-01.

Glycolic acid: JT Baker, Catalog No. M821-05.

Sodium hydroxide: 5.0 M NaOH aqueous solution Sigma Aldrich, Catalog No. 58263-150 ml.

Potassium hydroxide: 0.1 M KOH in methanol (BDH).

Ethanol: 200° Proof Sigma Aldrich, Catalog No. 459844-1L.

Microfiber chitin: ~10 micron diameter of aspect ratio ~100/1 of 100% acetylated. Weifang Centrifugal spun chitosan nanofiber Lot G01 of basis weight 12 g/m²

Tricol Medical Grade non-woven microfiber.

De-ionized water: Ricca ACS Reagent Grade deionized water, Catalog No. 9152-5.

Acetic anhydride: ACS reagent grade obtained from Sigman Aldrich, Catalog No. 320102-1L.

3,4-dihydroxyhydrocinnamic acid (Mw=182.17 g/mo): 98% Sigma Aldrich, Catalog No. 102601.

1-ethyl-3-(−3-dimethylamino-propyl)-carbodiimide: (alternatively N-(3-dimethylaminopropyl)-N'-ethylcarbodiimide hydrochloride with common acronym EDC) Sigma Aldrich, Cat. #E7750.

Sodium Chloride: Sigma Aldrich, Catalog No. 793566-500 g.

Synthetic gastric solution: Pepsin—Sigma Aldrich P7000-25G, NaCl—Sigma Aldrich 793566-500G, H₂O ACS Reagent grade, NaOH—Sigma Aldrich, Catalog No. 58263-150 ml.

Tissue: fresh swine bladder mucosa, fresh swine stomach mucosa from Animal Biotech Industries Inc.

Citrated bovine whole blood: Lampire Biological Laboratory Bovine CPD, Catalog No. 7720010.

Cynaoacrylate: Permabond 910 Tissue Adhesive, Catalog No. 72590.

Dialysis Tubing: 3,500 Da MWCO Snakeskin Dialysis Tubing (Fisher Scientific), Cat. #P188244.

Pectin: MP Biomedicals LLC, Catalog No. 102587.

Glycerol: Sigma Aldrich, Catalog No. G-8773.

Polyethylene glycol: Spectrum, Catalog No. P0108.

Polyethylene oxide: Mw 400,000 da, Sigma Aldrich Catalog No. 372773-500G.

Poloxamer 407: Spectrum, Catalog No. P1166.

Guar: Sigma Aldrich, Catalog No. G4129.

Cellulose (microcrystalline powder): Sigma Aldrich, Catalog No. 435236.

Polyacrylic acid: My 1,250,000 Sigma Aldrich, Catalog No. 306215-100G.

HemCon Patch® Pro, highly effective commercial chitosan hemostatic dressings, were used as positive control dressing in acute hemostatic studies.

Standard surgical gauze was used as a negative control in acute hemostatic studies.

Example 1

Preparation of Catechol Chitosan and Characterization

Approach 1.

Chitosan A (9.0 g) was dissolved in deionized water (148 g) and HCl (28 ml, 1.0 M HCl). A 1:1 (150 ml) solution of water:ethanol was prepared. 3,4-dihydroxyhydrocinnamic acid (25.9 mmol) and N-(3-dimethylaminopropyl)-N'-ethylcarbodiimide hydrochloride (51.8 mmol) were dissolved in the water/alcohol solution. The water/alcohol solution was added to the chitosan solution. The solutions were vigorously mixed. The reaction mixture was controlled to pH 5.4 using dropwise addition of 0.1 M HCl and 0.1 NaOH solution and left to react with overhead stirring for at least 12 hours. Following this, the chitosan solution (~300 ml) was dialyzed against 5 liters of water acidified with 1 drop of 1.0 M HCl solution for six days and against non-acidified water for at least 3 hours. Dialysate was changed at −24 hour intervals throughout the duration of the dialysis with at least 5 changes of water.

Approach 2

Chitosan A (1.5 g) was dissolved in water (140 g) and HCl (5 ml, 1.0M HCl). A 1:1 solution (145 ml) of water: ethanol was prepared. 3,4-dihydroxyhydrocinnamic acid (10.5 mmol) and N-(3-dimethylaminopropyl)-N'-ethylcarbodiimide hydrochloride (13.0 mmol) were dissolved in the water/alcohol solution. The water/alcohol solution was slowly added to the chitosan solution and the reaction mixture was stirred with an overhead mechanical stirrer at low stirrer speed. The reaction mixture was controlled to pH 5.5 using dropwise addition of 0.1 M NaOH and 0.1 M NaOH solution and left to react for ~12 hours under stirring. After the reaction process, the solution was dialyzed as described in approach 1.

Approach 3

Chitosan A (9.0 g) was dissolved in water (126 g) acidified with HCl (30 ml, 1.0M). A 1:1 solution (150 ml) of water: ethanol was prepared with N-(3-dimethylaminopropyl)-N'-ethylcarbodiimide hydrochloride (31.3 mmol) dissolved in the water/alcohol solution. Following this, 3,4-dihydroxyhydrocinnamic acid (15.7 mmol) was dissolved in 15 ml of water and this solution was added slowly to the chitosan solution under moderate overhead mechanically stirring. The water/alcohol solution containing the N-(3-dimethylaminopropyl)-N'-ethylcarbodiimide hydrochloride was slowly added to the chitosan solution and the reaction mixture was stirred with an overhead mechanical stirrer at low stirrer speed. The reaction mixture was controlled to pH 5.5 using dropwise addition of 0.1 M KOH (in methanol solution) and 0.1 M HCl solution and left to react for ~12 hours under stirring. After the reaction process, the solution was dialyzed as described in approach 1.

Approach 4

Chitosan A (9.0 g) was dissolved in water (126 g) acidified with HCl (30 ml, 1.0M). The solution was then adjusted to near pH 5.1 using 0.1 M HCl and 0.1 M NaOH aqueous solution. A 1:1 solution (150 ml) of water: ethanol was prepared with N-(3-dimethylaminopropyl)-N'-ethylcarbodiimide hydrochloride (31.3 mmol) dissolved in the water/alcohol solution. Following this, 3,4-dihydroxyhydrocinnamic acid (15.7 mmol) was dissolved in 15 ml of water and this solution was added slowly to the chitosan solution under moderate overhead mechanically stirring. The water/alcohol solution containing the N-(3-dimethylaminopropyl)-N'-ethylcarbodiimide hydrochloride was slowly added to the chitosan solution and the reaction mixture was stirred with an overhead mechanical stirrer at low stirrer speed. The reaction mixture was controlled to pH 5.0 using dropwise addition of 0.1 M KOH (in methanol solution) and 0.1 M HCl solution and left to react for ~12 hours under stirring. After the reaction process, the solution was dialyzed as described in approach 1.

Degree of Substitution of Catechol Chitosan

Quartz UV test cells, 1 cm path length, ×2 (HACH Co., cat #48228-00) were used in acquiring UV/vis spectra. The UV/Vis spectrophotometer was a Varian Cary Bio 100.

Standard solutions of 3,4-dihydroxyhydrocinnamic acid were prepared in water and absorbance at 280 nm was plotted against concentration. The extinction coefficient in the Beer Lambert relationship shown below for absorbance in dilute solution $$A = \varepsilon \cdot c \cdot l$$

A is absorbance (dimensionless) and l is the path length (Absorbance <0.5) was determined as 2,540±50 liter/(mol·cm). This value was used to determine degree of substitution in the modified chitosan in dilute aqueous solution of known mass of modified chitosan, known volume of solution and measured peak absorbance at 280 nm.

The chitosan catechol solution is diluted so that its absorbance at 280 nm is less than 0.5 (usually about 1:50 or 1:100). The absorbance, the weight of the solution used in the dilution, and the percent solids (CS-catechol) were used to find the fractional degree of substitution ($f_{DS}$) of the HCA with respect to free amines on the chitosan backbone according to the equations:—

$$f_{DS} = \frac{n_{HCA}}{f_{DDA} \cdot n_{total\ Chitosan\ mers}}$$

$$f_{DS} = \frac{A \cdot V \cdot \{(f_{DDa} \cdot 161) + (1 - f_{DDA} \cdot 203)\}}{\varepsilon \cdot l \cdot \left\{ m_{cc} - \left( \frac{A \cdot V}{\varepsilon \cdot l} \cdot 165.17 \right) \right\} \cdot f_{DDA}}$$

where A is UV/vis absorbance at 280 nm of the modified chitosan; V is the volume (liters) of the modified chitosan solution taken to dry to constant dry mass; $m_{CC}$ is the measured dry mass (g) of the catechol modified chitosan; $f_{DDA}$ is the fractional degree of deacetylation of the chitosan.
Results The chitosan-catechol syntheses yielded 50-300 mL of chitosan catechol solution that ranged from milky to clear, light pink to brown, and with viscosity ranging from thin liquid consistency (e.g. water near 1 cps viscosity) to thick liquid consistency (e.g. honey: viscosity >100,000 cps). The synthetic results (see Table 1) were dependent on the initial concentration of chitosan, avoidance of precipitation of chitosan in the pH adjustment step from near pH 2 to pH 5, maintenance of pH near 5.0 to 5.5 during reaction, and thorough removal of low molecular weight components in the dialysis washing step.

TABLE 1

| Summary of Characterization Results | | |
| --- | --- | --- |
| Cs-Cat Approach | Percent Solids (w/w)[¶] | Percent Substitution |
| 1 | 0.72 ± 0.1 | 17.2 ± 2 |
| 2 | 0.42 ± 0.1 | 132* |
| 3 concentrated† | 0.63 ± 0.1 | 29.0 ± 3 |
| 4 concentrated† | 1.80 ± 0.1 | 26.4 ± 3 |

[¶]Percentage dry solid in the solution was determined gravimetrically
*Synthesis in approach 2 resulted in excessive Uv/vis absorbance in determination of degree of substitution
†Catechol chitosan was concentrated by heat assisted drying removal of water from the solution suspended within its dialysis membrane.

Example 2

Freeze Phase Separated Hydrophilic Polymer Dressings

Hydrophilic polymer aqueous solutions were prepared inside 500 ml, 1000 ml or 2000 ml Nalgene LDPE bottles or polypropylene beakers by addition of components including, but not limited to, pre-prepared solution, hydrophilic polymer, water, acid, and additional components. FIGS. 8A-8B list formulation approaches, hydrophilic polymers, and % w/w of solution hydrophilic polymer components. Some of the formulations in FIGS. 8A-8B do not contain chitosan. Formulation strategies are listed in FIGS. 8A-8B as A, B, C, D, E, F, and G. Strategy A was primarily as a control of materials such as chitosan which were expected not to resist dissolution in the stomach as tested by in vitro simulated gastrointestinal fluid. Reacetylation (Strategy B) was one of the proposed strategies to reduce rate of dissolution/degradation until in vitro simulated gastrointestinal fluid testing in the presence of pepsin demonstrated faster rate of degradation and dissolution of chitosan with lower degree of deacetylation. Strategy C was investigation of compositions of known polysaccharides (guar, pectin and starch) without chitosan which resist in vitro simulated gastrointestinal fluid digestion. Strategy D was strategy C with chitosan and possibly other hydrophilic polymers. Strategy E was use of catechol modified chitosan as the only hydrophilic polymer. Strategy F was use of catechol modified chitosan with other hydrophilic polymers. Strategy G was use of a centrifugal spun chitosan fiber.

The main problems experienced when formulating for the gastrointestinal hemostatic dressing application were: (1) unexpected and rapid (<10 mins) pepsin promoted degradation of chitin and chitosan in synthetic gastric fluid, wherein pepsin promoted a rate of chitosan degradation at increasing rates corresponding with lower degrees of deacetylation; (2) unexpected interference from blood in achieving adherence with the pure catechol modified chitosans; (3) susceptibility in dressing cracking and tearing when making changes to formulations to address other problems.

The final hydrophilic polymer solution % w/w was between 0.1% to 4% polymer. Capped bottles and their contents were mixed continuously at room temperature over 12 to 24 hours to achieve full solution homogeneity using IKA KS260 orbital shaker or a Wheaton bench top bottle roller. Beaker solutions were mixed on a magnetic stirrer plate with magnetic stirrer bead at room temperature for 12 to 24 hours to achieve solution homogeneity. Parafilm was used to close the beaker from the external environment during mixing. The solutions prepared for freeze phase separation were substantially homogeneous and clear when suspension conditions were not present (exceptions with A06, B02, B04 and C05). The catechol chitosan solutions demonstrated some haze and milky appearance indicating presence of some dispersed fine catechol chitosan globular particles.

Except in the case of Strategy G, chitosan solutions were prepared as freeze phase separated dressings with final solution % weight of hydrophilic polymer in the range 0.25% to 4% w/w aqueous solution. Freeze phase separation was performed in Teflon coated aluminum mold wells with horizontal flat bases. The solutions were poured into the wells to a height from the mold base of preferably not more than about 10 mm, more preferably 2.5 mm and most preferably 5.0 mm. The solutions initially at a temperature in the molds before freezing between 15° C. and 30° C. were then frozen by application of cooling through the base of the molds. Although other cooling temperatures may be applied to achieve suitable freeze phase separated structure, preferably the applied cooling temperature of the shelf was −40° C., more preferably the cooling temperature was −55° C. and most preferably the cooling temperature was −45° C. After the solution achieved freezing phase separation and the temperature of the frozen solution equilibrated at the freezing temperature, the system was allowed to further freeze phase separate and equilibrate for at least an additional hour before drying. In a modified freezing and mold filling method to accommodate layers of different freeze phase separated solutions, a first layer was added to the mold to a preferred depth and frozen, a second layer was then added and frozen, a multi-layered freeze phase separated dressing could be prepared in this manner. Care was needed to ensure there was no frost between an (n−1)th frozen and nth poured solution and differences in layer frozen structure could result in cracking. The discovery of the successful method of layering and adhering of single layer previously freeze dried hydrophilic polymer matrices to a single co-adhered compressed multilayered composite sheet during this investigation was an unexpected and significant finding. It is also possible to combine separately prepared freeze dried compositions using compression.

A 24 square foot shelf Virtis Benchmark 2000 pilot scale freeze dryer was used for sublimation freeze drying of the freeze phase separated frozen solution plaques. In the primary freeze drying (removal of ice not hydrogen bonded to the hydrophilic polymers), the equilibrated frozen plaques in their molds were subjected to reduction in pressure ≤300 mTorr within the freeze dryer, the freeze dryer condenser was set to ≤−65° C. and the freeze dryer shelves were heated to promote sublimation of the ice from the freeze separated plaques without increasing plaque temperature above −15° C. After removal of substantially all the non-bonded ice, the shelf temperature was raised to near 25° C. for removal of the hydrogen bonded ice and reduction of moisture content in the dried dressing to not more than about 4% residual water in the dried dressing. Final dried matrices conformed to the original shape of the filled mold with close to 5% shrinkage in length and width and density between 0.005 $g/cm^3$ and 0.04 $g/cm^3$. They contained void space of more than 95% and they were interconnected porous structure (e.g., 20-300 micron) with fine polymer lamella (e.g., submicron to 5 micron thickness) and pore spacing between adjacent lamella of, for example, 20 microns to 300 microns.

After freeze phase separation and drying, the dried matrices were compressed from their original thicknesses (10 mm to 2.5 mm) to a final thickness preferably near 50 microns. If two uncompressed dressings were compressed one on top of the other then they would be permanently bonded together at the conclusion of the compression process. Calibrated uniform thickness thin shims may be used in the compression to achieve a desired thickness of compressed dressing substantially the same thickness as the shim. There are a number of ways to achieve this compression with a desired compression set near 50 microns. The preferred compression method used in the investigation was compression of the whole dried uncompressed dressing (dimensions typically close to 100 mm long×100 mm wide×2.5 mm high or 50 mm diameter×2.5 mm high) with uniaxial compression rate at ≤10 mm/min, or about ≤0.5 mm/min, to ≤100 microns thickness between aligned platens. While lower compression rates lead to better mechanical properties of the final dressings, dressings prepared with initial compression rates near, for example, about 10 mm/min are acceptable. The platens (Teflon coated Mic 6 Aluminum 300 mm×300 mm×90 mm) were machined to flat planar faces (≤5 microns in 300 mm). The temperature of platens during compression was maintained preferably near 80° C. over 3 to 5 minutes of uniaxial compression. Compression was achieved by screw loading at the four corners of the platens at up to four tonnes (tonnes meaning 1000 kilograms) loading at each corner. Compression was held for at least 2 minutes before release of load. The novel compressed hydrophilic polymer matrices were measured for compression thickness and weight. Final densities were between 0.35 and 0.55 $g/cm^3$. After compression, the dressings were further processed. This additional processing included die cutting into 2.5 cm diameter test pieces and in some cases thermal annealing heat treatment (heated in a convection oven at 60° C. to 150° C. for 5-30 minutes). At the conclusion of processing the dressings were placed in foil pouches with thermal sealing. Packaged dressings intended for animal and biocompatibility testing were gamma-irradiated at 25 kGy.

Example 3

In Vitro Testing of Gastrointestinal Hemostatic Dressing Prototypes

Synthetic Gastric fluid preparation: Pepsin (1.6 g), NaCl (1 g), water (500 ml) was added to a Nalgene LDPE 1000 ml bottle and mixed. The acidity was adjusted to be between pH 3 to 4 using Millipore pH 0-14 universal indicator strips and dropwise addition of 3.0 M HCl. Dropwise addition of 1.0 M NaOH was used to raise the pH if required.

1. Test Tube Method

For rapid screening of test article resistance to dissolution/fragmentation in synthetic gastric fluid, a 0.5 cm×0.5 cm piece of test article sheet was added to the base of a labeled 15 ml Falcon tube and 5 ml of gastric fluid was added to the tube before capping and placing upright in an incubator at 37° C. with gentle shaking. The tube was monitored until demonstrable dissolution/fragmentation of the sample was observed and the time to dissolution/fragmentation was recorded. The results of test tube testing are provided in FIGS. 6A-6C.

2. Beaker Method

For materials showing resistance in the test tube test, a modified test method was developed whereby a 38 mm×38 mm piece of fresh stomach mucosa was adhered inside a polystyrene beaker (250 ml, Fisher Catalog No. 08-732-124) at its base using a thin layer of cyanoacrylate adhesive applied using a cotton swab. The mucosa surface prior to gluing was dabbed dry using Texwipe tissue. The adhesive was allowed to dry over 2-5 minutes. After becoming fully adhered to the beaker, the top exposed tissue surface was wetted drop-wise (generally 2 drops) with citrated whole bovine blood, and a 20 mm×20 mm piece from a test article sheet was adhered to the blood covered mucosa surface by application of 500 g of load applied orthogonally to the mucosa surface for 1 minute through a 25 mm diameter PVC flat head probe. Synthetic gastric fluid at room (~90 ml) was added to the beaker. Parafilm was used to seal the beaker and the beaker was placed upright on an IKA KS260 orbital shaker in an incubator at 37° C. under mild shaking (130 rpm). The inside of the beaker was monitored at minutes and then hourly until demonstrable separation from mucosa and/or dissolution/fragmentation of the sample was observed and the time to separation/dissolution/fragmentation was recorded.

During test method development, the load applied (up to 5 kg) and time of application for attachment was up to 5 minutes. In comparison to minimally invasive in vivo application the gastrointestinal surgery team advised that an application not be more than 300 g load applied uniformly over a 2.5 cm diameter dressing for not more than 30 seconds. The original conditions of 5 kg and 120 seconds were modified to 500 g for 1 minute. The application of 300 g load for 30 seconds application is now applied. Results of beaker testing are provided in FIGS. 6A-6C.

3. Mechanical Fold Testing

Sample sheets were folded 180° along length and width axes and the crease line was compressed. Dry test sheets (25 mm×25 mm) were folded and unfolded and observation of resistance to tearing and cracking was recorded. Results of fold testing are provided in FIGS. 6A-6C.

4. Mechanical Tissue Adherence

A uniaxial mechanical tester (Instron Model 5844) with 10 N load cell was used to investigate wet adhesion to mucosa. Adhesion testing was performed using ASTM F2258-03 "Standard Test Method for Strength: Properties of Tissue Adhesives in Tension". Testing was performed with a testing configuration with lower and upper PVC probes uni-axially aligned in the z vertical direction so that the edges of their x-y horizontal, 15.2 mm diameter faces would accurately (±0.2 mm) coincide with each other with uniaxial lowering of the top probe which was supported on the upper, movable Instron crosshead in chuck fixture. The lower PVC probe was supported in a stationary, bottom, chuck fixture. The bottom PVC horizontal surface was used to support a 10 mm×10 mm mucosal tissue sample adhered at least 5 minutes before testing by cyanoacrylate glue to the PVC surface. The top PVC horizontal surface was used to support a 10 mm×10 mm CGHD test piece that was adhered by a 3M double side tape at least 5 minutes before testing. The square tissue piece was wetted with 0.25 ml of the de-citrated bovine whole blood CPD prior to lowering the probe onto the test surface. The probe was lowered at 10 mm/min until a maximum load of 0.98 N was reached. At contact, the test and tissue pieces contacted accurately (±0.2 mm) and were mutually co-planar. The uniaxial probe load at 0.98 N was maintained for 30 seconds after which the probe was removed at 10 mm/min and maximum failure stress was recorded. The results of adherence testing are shown in Table 2.

TABLE 2

| | Probe Adherence Results | | |
| | G01-Nanospun CS (6-layer) (kPa) | F11-25% CS-cat, 22-1 conc'd/2% CS AcOH soln (kPa) | PV Probe (No Dressing) (kPa) |
| --- | --- | --- | --- |
| 1 | 0.86 | 2.07 | 0.30 |
| 2 | 1.47 | 3.53 | 0.26 |
| 3 | 2.13 | 4.46 | 0.08 |
| 4 | 1.82 | 6.82 | 0.25 |
| 5 | 0.92 | 3.69 | |
| Mean | 1.44 | 4.11 | 0.22 |
| Std. Dev. | 0.55 | 1.74 | 0.10 |

Example 4

In Vivo (Swine Model of Upper Gastrointestinal Bleeding) Screening Study

Animals

A total of 4 crossbred adult domestic swine, body weight from 40 to 50 kilograms, were used in this study.

All experiments were performed in accordance with the 2011 National Research Council, "Guide for the Care and Use of Laboratory Animal" and applicable federal regulations. The protocol for the animal is in accordance with the NIH Guidelines for the Care and Use of Laboratory Animals and was approved by the Institutional Animal Care and Use Committee. All procedures and care of the animals were performed at the approved animal research facility.

Veterinary staff inspected all of the animals to ensure baseline health. Animals were removed from all bedding 72 hours prior to the procedure and not permitted food 24 hours prior to surgery. Animals were allowed to drink water ad libitum. Twenty minutes prior to the procedure, the animals were given 500 mg of intravenous Cefotetan and a 250 ml fluid bolus of Ringer's Lactate. After premedication with glycopyrrolate and a combination of tiletamine HCl and zolazepam HCl (Telazol®, Fort Dodge Laboratories, Fort Dodge, Iowa), anesthesia was induced by mask using 5% isoflurane. The swine was intubated, placed on a ventilator, and maintained with 2-3% isoflurane with endotracheal intubation. The right femoral artery was surgically isolated and cannulated with a 6 Fr catheter to facilitate continuous blood pressure monitoring and retrieval of blood for laboratory studies. To induce a state of coagulopathy, 5000 units of heparin, was given intravenously (IV). A continuous infusion of heparin of 50 units/kg was used during the procedure to maintain anticoagulation. An activated clotting time (ACT) level was tested after 10 minutes and then every 20 minutes during the procedure with additional heparin (50% of the original dose, 2500 units) given IV as needed to maintain ACT >250 seconds anticoagulation. ECG, blood pressure, and oxygen saturation were monitored during surgery and recovery. Vitals including blood pressure, % isoflurane, 02 flow, respiratory rate, heart rate, SpO2, capillary refill time, blood pressure and mean arterial pressure, and body temperature were recorded every 15 minutes.

At the completion of the experiment, while under anesthesia, the animals were euthanized with IV administration of Euthasol (1 mg/10 lbs). Death was confirmed by flat-wave ECG and absence of heart beat by stethoscope.

Gastric Bleeding Model

The swine were prepared using Chlorhexadine and draped in a sterile fashion. A midline laparotomy was performed to expose the stomach. A 5-cm segment of the gastroepiploic vessels were dissected free from the gastric wall. For each segment, a 1-cm gastrotomy was made adjacent to the free but intact blood vessels. The artery was then pushed through the gastrotomy and positioned so that it is exposed to the gastric lumen. The gastric incision was then closed in a standard manner along with the abdominal wall. An upper endoscopy (GIF Type Q180, Olympus) was performed to identify the gastric wound site in the stomach. The wound site and gastric vessels were then located and incised with an endoscopic biopsy forceps to create a pulsatile bleeding.

The chitosan gastrointestinal hemostatic dressings (CGHD) identified in Table 3, below, were applied with manual application by hand. In brief, an approximate 12 cm incision was made on anterior gastric wall to expose gastric cavity and to apply the CGHD prototype dressing (20 mm×20 mm) on the gastric bleeding site. Before dressing application, bleed rate was determined using dry pre-weighed folded gauze sponges to absorb any blood from the wound over a 15 second period and weighed, multiplied×4 to calculate bleed rate (weight of blood) per minute. The CGHD dressing was placed over the wound with a gauze sponge on top. Manual pressure is applied evenly with light pressure near 200-300 g over the patch for 30 seconds. At 30 seconds the gauze was removed and the area was observed for initial hemostasis and followed for signs of rebleeding for up to 10 minutes. At completion of application, the CGHD dressing was removed and dressing tissue adherence was ranked according to an adherence score in accordance to how the dressing adhered to tissue surface using the Adherence Score System (Table 3).

TABLE 3

Adherence Score

| Score | Description |
|-------|-------------|
| 0 | No adherence |
| 1 | Little adherence |
| 2 | Moderate adherence |
| 3 | Moderate to strong adherence |
| 4 | Strong adherence |

Results

| Type of Dressing | Code# | Gastric Vascular Injury | | |
|------------------|-------|------------------------|----------------|----------------|
| | | Bleed rate (g/min) | Hemostasis Rate (%) | Adhesion score |
| 4Ch01.Pect | D24 | 8 | 70% | 2 |
| ChCatechol | E1 and E2 | NA | 29% | 2.5 |
| 0.25Cat1.5Ch | F11 | NA | 63% | 2 |
| 0.75Cat0.5Ch | F12 | NA | 50% | 1.5 |
| Nanofiber 12GSM | G01 | 5 | 67% | 1 |
| Patch Pro | H01 | NA | 100% | 3.5 |
| Gauze | H02 | 13 | 33% | 0 |

Three CGHD family prototypes (D24, F11, and G01) demonstrated good hemostatic properties in terms of immediate hemostasis and acceptable adhesion scores in the gastric vascular injury model. Slow wound tissue adherence for pure catechol modified chitosan was addressed by combination of unmodified chitosan with the catechol chitosan. Final heat treatment of these compressed freeze phase separated dressings for 15 minutes to 30 minutes at close to 80° C. resulted in dressings with good immediate tissue adherence and thus promising hemostatic performance in rapidly controlling pulsatile hemorrhagic gastrointestinal bleeding with short (30 seconds) low pressure applications. It is noted that the Patch Pro is not suitable for use in the gastroscope delivery as it cannot be folded as required and is too thick. Also, the Patch Pro is formed of standard chitosan which is degraded in about 15 minutes or less in the upper GI.

Example 5

In Vivo (Swine Model of Upper Gastrointestinal Bleeding) 3 Hour Study

Animals

A total of 4 crossbred adult domestic swine, body weight from 40 to 50 kilograms, were used in this study.

Animal preparation, surgical preparations, animal anesthesia and animal sacrifice were the same as presented in Example 4.

Gastric Bleeding Model

Figure 2:
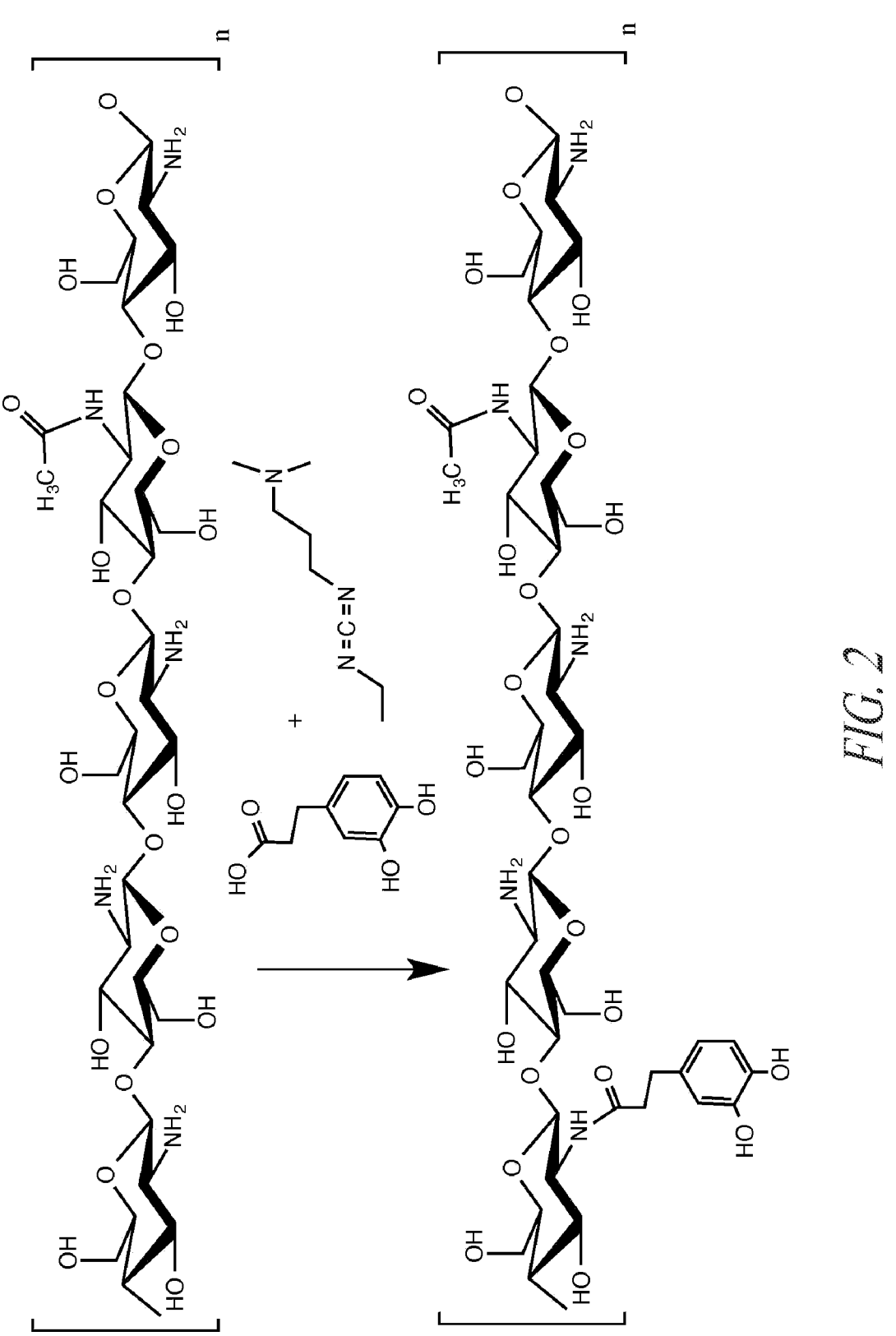
FIG. 2 depicts an N-acylation addition reaction in the presence of 1-ethyl-3-(-3-dimethylamino-propyl)-carbodiimide (EDC) where 3,4-dihydroxyhydrocinnamic is covalently attached to a chitosan C-2 amine with a degree of substitution of 25% in aqueous solution at pH 5.5.
Figure 3:
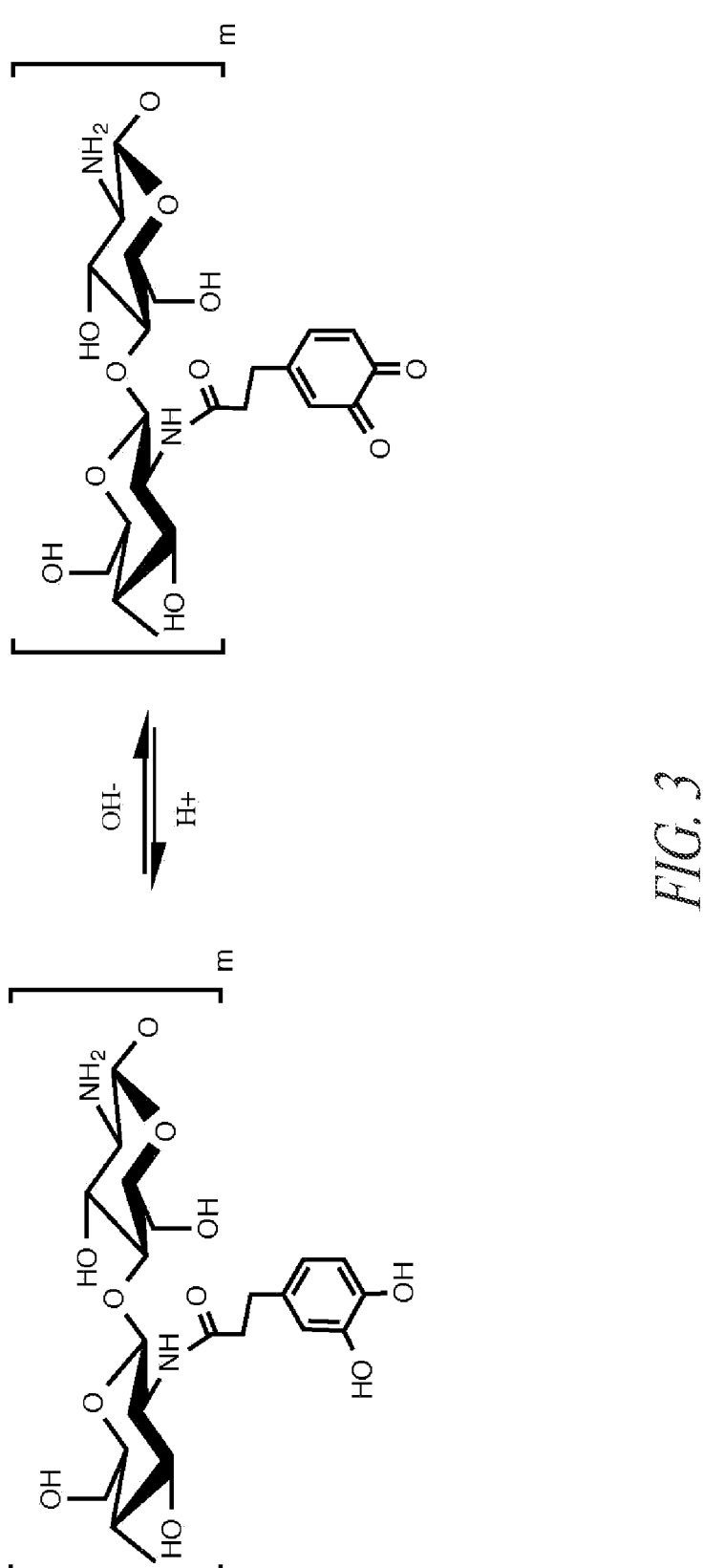
FIG. 3 depicts oxidation of catechol modified chitosan to ortho-quinone modified chitosan under elevated pH and in the presence of oxygen
Figure 4:
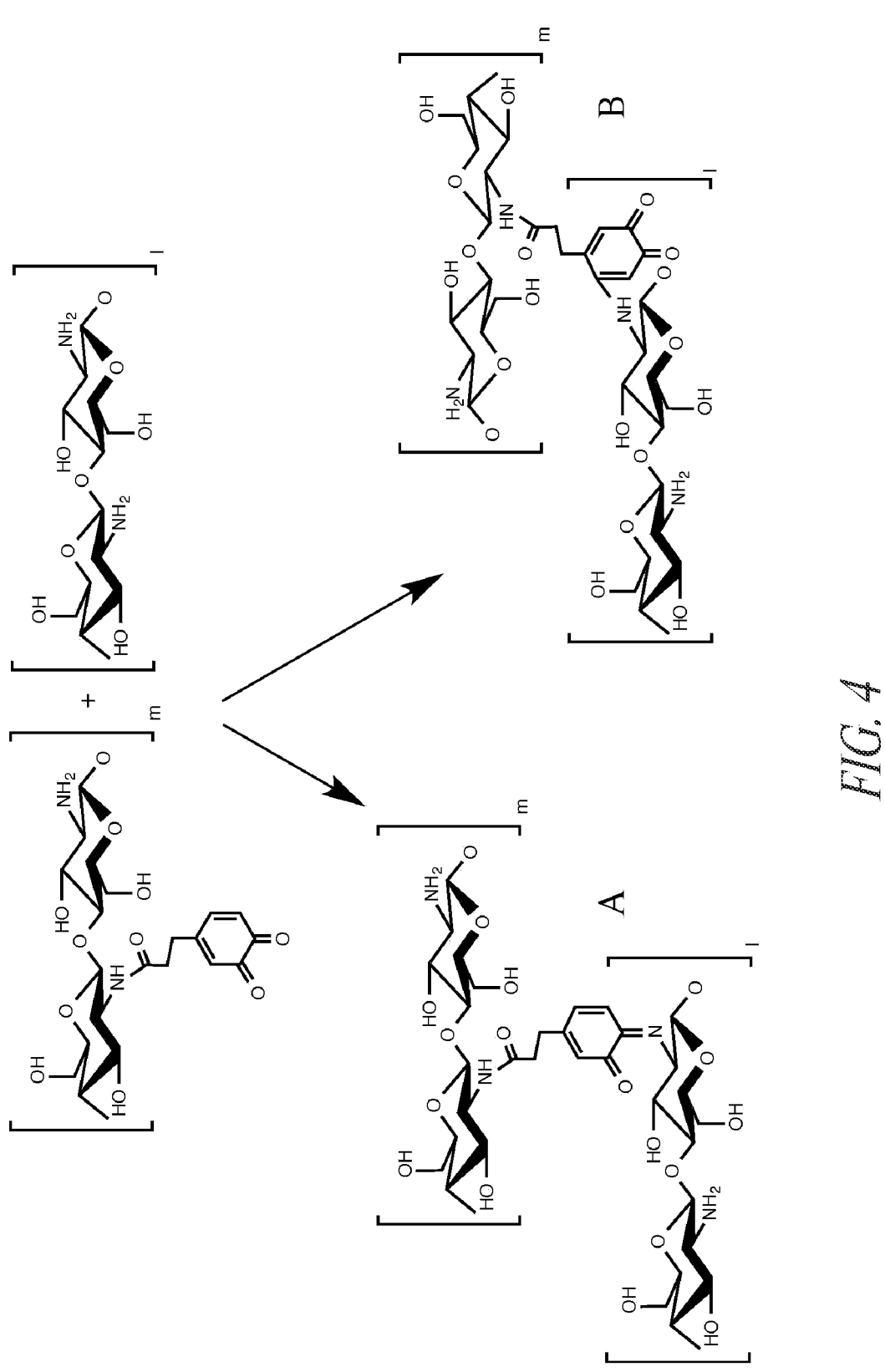
FIG. 4 depicts Schiff base (A) and Michael addition (B) reactions causing crosslinking between catechol modified chitosan and chitosan.

The swine are prepared using Chlorhexadine and draped in a sterile fashion. A midline laparotomy was performed to expose the stomach. Two 5-cm segment of the gastroepiploic vessels were dissected free from the gastric wall. For each segment, a 1-cm gastrotomy was made adjacent to the free but intact blood vessels. The artery was then pushed through the gastrotomy and positioned so that it is exposed to the gastric lumen. The gastric incision was then closed in a standard manner along with the abdominal wall (FIG. 2).

An approximate 12 cm incision was made on anterior gastric wall to expose gastric cavity. The wound site and gastric vessels were then located and incised with a forceps to create a pulsatile bleeding. Before applied, the dressing bleed rate was determined using premeasured folded gauze sponges to absorb any blood from the wound over a 15 second period and weighed, multiplied×4 to calculate bleed rate. The CGHD dressing was then placed over the bleed wound with a gauze sponge on top. Manual pressure is applied evenly over the patch for 30 seconds. At 30 seconds the gauze was removed and the area was observed for hemostasis initially and for up to 10 minutes. After 10-minutes observation, if achieved hemostasis, the gastric incision was closed in a layer fashion, i.e., wherein the surgeon sutures incised layers together consecutively. Then the abdominal wall was closed for 3-hours observation. At completion of 3-hours application, an upper endoscopy (GIF Type Q180, Olympus) was performed to identify the wound dressings for a visual examination. Then the incisions of abdomen and stomach were reopened for gross examination of the dressings. The CGHD dressings were removed and gave an adhesion score in accordance to how the dressing adhered to tissue surface using the Adherence Score System (Table 3).

At completion of these procedures, the wound sites were re-prepared by removal of old clots and residual of wound dressing to re-applied second sets of dressing as described above. Each wound site was used to test 2 dressings in this study phase.

Bleed Rate

Metzenbaum scissors were used to make a semi-transected vascular injury at gastric vessels to create a pulsatile bleeding. Bleed rate was measured with a pre-weighed gauze and recorded in g/min. Bleed rate for each injury was determined and recorded prior to dressing application. Test Pieces were 20 mm×20 mm.

Eight dressings were tested from each type of Nanospun Chitosan (G01) and Chitosan Catechol Blend (F11).

Application of Test Pieces

The 30-second timer was started as the test piece was applied centrally over the injury and with sufficient pressure from fingers to stop bleeding. One piece of 50 mm×50 mm gauze was folded into two and applied over the 20 mm×20 mm test piece. Any subsequent pooled blood was suctioned from the site. After 30 seconds of light digital pressure (near 300 g load), fingers were removed and the test dressing observed for any sign of bleeding. If bleeding was observed, pressure was re-applied for 30 seconds. If hemostasis was achieved upon the release of the pressure, dressing was observed for 10 minutes. If there is no bleeding recurrence, the stomach wall was closed and observed through GI scope for 3 hours. If there was no bleeding recurrence after 3 hours, the dressing test piece was considered successful. If bleeding recurred within 5 minutes, the dressing was removed and a new dressing applied. Up to two reapplications were utilized.

TABLE 4 below summarizes the result of the study.

| Dressing Code# | # of dressing passed | | | # of dressings tested | % success |
|----------------|---------|---------|---------|-----------------------|-----------|
| | 1st app | 2nd app | 3rd app | | |
| F11 | 3 | 1 | 2* | 13 | 46 |
| G01 | 0 | 3** | 1* | 12 | 31 |

*1 dressing from each group had extra dressing to stop oozing after $3^{rd}$ pressure application
**1 dressing was held for extra 30 seconds

Nanospun chitosan dressing (G01) had 4 successful application out of 12 dressings applied. While the 25% catechol/75% 2% chitosan dressing (F11) had 6 successful application out of 13 dressings tested. Two deviations were noted for the dressing applications: one dressing from each group had extra dressing to stop oozing that did not stop on swine #4; and one of nanospun chitosan dressing was held for extra 30 seconds.

On all applications, an endoscope was inserted to evaluate if the dressing was still present and hemostatic. In all cases, all dressings were confirmed as present, hemostatic and visible through the scope. After more than 3 hours of dressing application, the stomach was opened to allow the injury sites and dressings to be examined. All dressings were intact. Clot formation was observed on all wounds. It was noted in all cases of initial dressing success that there was no subsequent bleeding observed from the wounds at the 3 hour timepoint.

The final best dressing prototypes identified through testing in Examples 3, 4, and 5 demonstrated prolonged efficacy once they were adhered under light manual pressure with short duration application hold necessary for delivery through a standard gastroscope delivery port. The best dressings that were developed were amenable in a folded (or furled) configuration to be delivered through a standard diameter 2.8 mm diameter delivery channel from a standard gastroscope.

ALL CGHD DRESSINGS THAT ACHIEVED SUCCESSFUL HEMOSTASIS (COMPLETE CESSATION OF BLEEDING) IN THE FIRST 10 MINUTES OF APPLICATION WITH NO MORE THAN 3×30 SECOND HOLD APPLICATIONS REMAINED FULLY HEMOSTATIC THROUGH THE 3 HOUR TEST PERIOD INSIDE THE CLOSED PORCINE STOMACH. SUCCESS WAS ACHIEVED FOR 31% OF G01 PROTOTYPE APPLICATIONS AND FOR 46% OF THE F11 PROTOTYPE APPLICATIONS. THE CHALLENGING NATURE OF THIS STUDY MADE SUCCESS NEAR 50% (I.E. F11 PROTOTYPE) RELEVANT TO CLINICAL APPLICATION ESPECIALLY WHEN IT IS NOTED THAT ALL INITIAL SUCCESSFUL MUCOADHESIVE APPLICATIONS RESULTED IN 100% SUCCESS IN THE LONGER TERM. THE MIXED CHITOSAN AND CATECHOL CHITOSAN DRESSINGS PROVIDE FOR SUBSTANTIAL RESISTANCE TO DIGESTIVE FLUID DIGESTION, ARE ABLE TO BE FOLDED/FURLED INTO THE MOST COMPLEX AND COMPACT FORMS, AND PROVIDE FOR GOOD ADHESIVE PROPERTIES IN CONJUNCTION WITH MIXING WITH UNMODIFIED CHITOSAN

REFERENCES

The following is a list of references listed by number and corresponding to the bracketed numbers noted throughout this specification.

1. HCUP, Outcomes by 153 Gastrointestinal hemorrhage, in U.S. Department of Health and Human/HCUPnet2014, U.S. Department of Health and Human Services: Washington D.C.
2. Rockey, D. C., Gastrointestinal bleeding. Gastroenterol Clin North Am, 2005. 34(4): p. 581-8.
3. Crooks, C. J., West, J., and Card, T. R., Upper gastrointestinal haemorrhage and deprivation: a nationwide cohort study of health inequality in hospital admissions. Gut, 2012. 61(4): p. 514-20.
4. Jairath, V., Kahan, B. C., Logan, R. F., Hearnshaw, S. A., Travis, S. P., Murphy, M. F., and Palmer, K. R., Mortality from acute upper gastrointestinal bleeding in the United kingdom: does it display a "weekend effect"? Am J Gastroenterol, 2011. 106(9): p. 1621-8.
5. Sung, J. J., Tsoi, K. K., Ma, T. K., Yung, M. Y., Lau, J. Y., and Chiu, P. W., Causes of mortality in patients with peptic ulcer bleeding: a prospective cohort study of 10,428 cases. Am J Gastroenterol, 2010. 105(1): p. 84-9.
6. Jairath, V., Kahan, B. C., Stanworth, S. J., Logan, R. F., Hearnshaw, S. A., Travis, S. P., Palmer, K. R., and Murphy, M. F., Prevalence, management, and outcomes of patients with coagulopathy after acute nonvariceal upper gastrointestinal bleeding in the United Kingdom. Transfusion, 2013. 53(5): p. 1069-76.
7. Elta, G. H., Approach to the patient with gross gastrointestinal bleeding. Textbook of Gastroenterology, 2003. In: Yamada T., Alper, D. H., Editors (Lippincott Williams and Wilkins): p. 698-723.
8. Boonpongmanee, S., Fleischer, D. E., Pezzullo, J. C., Collier, K., Mayoral, W., Al-Kawas, F., Chutkan, R., Lewis, J. H., Tio, T. L., and Benjamin, S. B., The frequency of peptic ulcer as a cause of upper-GI bleeding is exaggerated. Gastrointest Endosc, 2004. 59(7): p. 788-94.
9. Jairath, V., Martel, M., Logan, R. F., and Barkun, A. N., Why do mortality rates for nonvariceal upper gastrointestinal bleeding differ around the world? A systematic review of cohort studies. Can J Gastroenterol, 2012. 26(8): p. 537-43.
10. Sheibani, S., Kim, J. J., Chen, B., Park, S., Saberi, B., Keyashian, K., Buxbaum, J., and Laine, L., Natural history of acute upper GI bleeding due to tumours: short-term success and long-term recurrence with or without endoscopic therapy. Aliment Pharmacol Ther, 2013. 38(2): p. 144-50.
11. Adler, D. G., Leighton, J. A., Davila, R. E., Hirota, W. K., Jacobson, B. C., Qureshi, W. A., Rajan, E., Zuckerman, M. J., Fanelli, R. D., Hambrick, R. D., Baron, T., and Faigel, D. O., ASGE guideline: The role of endoscopy in acute non-variceal upper-GI hemorrhage. Gastrointest Endosc, 2004. 60(4): p. 497-504.
12. Banerjee, S., Cash, B. D., Dominitz, J. A., Baron, T. H., Anderson, M. A., Ben-Menachem, T., Fisher, L., Fukami, N., Harrison, M. E., Ikenberry, S. O., Khan, K., Krinsky, M. L., Maple, J., Fanelli, R. D., and Strohmeyer, L., The role of endoscopy in the management of patients with peptic ulcer disease. Gastrointest Endosc, 2010. 71(4): p. 663-8.
13. Peng, Y. C., Chen, S. Y., Tung, C. F., Chou, W. K., Hu, W. H., and Yang, D. Y., Factors associated with failure of initial endoscopic hemoclip hemostasis for upper gastrointestinal bleeding. J Clin Gastroenterol, 2006. 40(1): p. 25-8.
14. Peng, Y. C., Tung, C. F., Chow, W. K., Chen, S. Y., and Chang, C. S., Factors contributing to the failure of argon plasma coagulation hemostasis in patients with nonvariceal upper gastrointestinal tract bleeding. Hepatogastroenterology, 2010. 57(101): p. 781-6.
15. Karaman, A., Baskol, M., Gursoy, S., Torun, E., Yurci, A., celikbilek, M., Guven, K., Ozbakir, O., and Yucesoy, M., Endoscopic topical application of ankaferd blood Stopper® in gastrointestinal bleeding. Journal of Alternative and Complementary Medicine, 2012. 18(1): p. 65-68.
16. Halkerston, K., Evans, J., Ismail, D., Catnach, S., Chaudhary, R., Fullard, M., King, A., and Leahy, A., PWE-046 Early Clinical Experience of Endoclot™ in the Treatment of Acute Gastro-Intestinal Bleeding. Gut, 2013. 62(Suppl 1): p. A149.

17. Holster, I. L., Kuipers, E. J., and Tjwa, E. T. T. L., Hemospray in the treatment of upper gastrointestinal hemorrhage in patients on antithrombotic therapy. Endoscopy, 2013. 45(1): p. 63-66.

18. Sung, J. J. Y., Luo, D., Wu, J. C. Y., Ching, J. Y. L., Chan, F. K. L., Lau, J. Y. W., MacK, S., Ducharme, R., Okolo, P., Canto, M., Kalloo, A., and Giday, S. A., Early clinical experience of the safety and effectiveness of Hemospray in achieving hemostasis in patients with acute peptic ulcer bleeding. Endoscopy, 2011. 43(4): p. 291-295.

19. Yau, A. H. L., Ou, G., Galorport, C., Amar, J., Bressler, B., Donnellan, F., Ko, H. H., Lam, E., and Enns, R. A., Safety and efficacy of Hemospray® in upper gastrointestinal bleeding. Canadian Journal of Gastroenterology and Hepatology, 2014. 28(2): p. 72-76.

20. Kheirabadi, B. S., Mace, J. E., Terrazas, L B., Fedyk, C. G., Estep, J. S., Dubick, M. A., and Blackbourne, L. H., Safety Evaluation of New Hemostatic Agents, Smectite Granules, and Kaolin-Coated Gauze in a Vascular Injury Wound Model in Swine. Journal of Trauma and Acute Care Surgery, 2010. 68(2): p. 269-278.

The invention claimed is:

1. A chitosan dressing comprising a catechol modified chitosan for use in the treatment of gastrointestinal tract bleeding, wherein the dressing is biocompatible, hemostatic, resists dissolution in gastrointestinal fluid having a pH of between 3.0 to 4.0 at about 37° C. for at least 6 hours, foldable, compressed, and has a thickness that is between about 50 microns to 500 microns, wherein the chitosan dressing adheres to wet gastrointestinal tissue when in a wet condition with an adherence strength between about 1 kPa and 7 kPa and seals and protects a target tissue site for 12 hours, achieves a controlled, slow dissolution from the attachment site over a period of time not exceeding seven (7) days, and has a brown coloration, including a dark brown coloration, and a density that is in the range of about 0.08 g/cm$^3$ to about 1.2 g/cm$^3$.

2. The chitosan dressing according to claim 1, wherein the dressing has a density that is in the range of about 0.35 g/cm$^3$ to about 0.55 g/cm$^3$.

3. The chitosan dressing according to claim 1, wherein the dressing has a strength of 5 MPa to 25 MPa UTS (ultimate tensile strength) and is one of:

square, rectangular, circular, or circular petal shaped.

4. The chitosan dressing according to claim 1, wherein the chitosan dressing, when dry, has a moisture content of 15% or less by weight (w/w).

5. The chitosan dressing of claim 4, wherein at least one of: (i) the adhesive side is provided on a first layer and the non-adhesive side is provided on a second layer; (ii) the adhesive side adheres to a tissue surface when the dressing is wet; (iii) the non-adhesive side does not adheres to a delivery device when the dressing is wet; and (iv) the dressing adheres to a gastrointestinal mucosa in 1 minute or less.

6. The chitosan dressing according to claim 1, wherein at least one of: (i) the dressing forms a quaternary ammonium cation at the chitosan glucosamine C-2 amine at a tissue site; and (ii) the catechol is oxidized to o-quinone and cross-linked in the chitosan dressing.

7. The chitosan dressing according to claim 1, further comprising at least one of spun fibers or a porous surface and wherein the porous surface provides one or more of an absorbent surface or channels to redirect moisture away from a target tissue surface site.

8. The chitosan dressing according to claim 1, wherein the dressing can be folded or furled without cracking or tearing, or wherein the dressing may, in an open, unfurled, or unfolded condition, have an outward facing surface area that is about four times greater to about six times greater than the outward facing surface area of that same dressing when it is in a closed, furled, or folded condition, or wherein the ratio of the outward facing surface area of an open, unfurled, or unfolded condition relative to a closed, furled, or folded condition ranges from about 2.1 to about 15:1 or wherein the dressing can be punctured or sewn without cracking or tearing.

9. The chitosan dressing according to claim 1, wherein the dressing is at least one of cross-linked or able to be delivered intact by a balloon device, a wire device, or an endoscopic device, and optionally, wherein the balloon device, the wire device, or the endoscopic device comprises a working channel having a diameter of one of between about 2.8 mm to about 4.5 mm, and wherein the dressing is delivered through the working channel.

10. The chitosan dressing according to claim 1, wherein the dressing is able to wet and adhere intact to gastric mucosa within 30 seconds with application of light pressure, and wherein the light pressure is about 200-300 g.

11. The chitosan dressing according to claim 1, wherein the chitosan dressing is able to at least two of: (i) remove hydrophilic and hydrophobic biological fluids that can interfere with adhesion; (ii) stay in place intact and stop moderate to oozing bleeding ranging from between about 20 ml/min to about 150 ml/min; (iii) readily detach from a delivery device after adherence to a target tissue site;; (iv) be unfolded; or (v) be furled and unfurled.

12. The chitosan dressing according to claim 1, wherein the dressing is at least one of not readily soluble in water, saline solution, blood, or GI fluid at about 37° C. for 12 hours following application, or not readily soluble in water, saline solution, blood, or GI fluid at about 37° C. for 24 hours following application.

13. The chitosan dressing according to claim 1, wherein the dressing does at least one of: (i) not adhere to a delivery device; (ii) not increase or decrease in size by more than about 25% in length and width, or more than about 50% in thickness in the presence of water, saline solution, blood, or GI fluid at about 37° C.; (iii) comprises an adhesive side that interacts with an injury site, and wherein the chitosan dressing comprises a non-adhesive side that interacts with one of a delivery device or the adhesive side when the dressing is in a dry and folded or a dry and furled condition.

14. The chitosan dressing according to claim 1, wherein the dressing is capable of being terminally sterilized without affecting dressing characteristics or is capable of being stored under controlled conditions over time without affecting dressing characteristics.

15. The chitosan dressing according to claim 1, wherein said treatment of a gastrointestinal tract bleeding, comprises at least one of directly adhering the dressing at an injury site upon wetting, and applying pressure to the dressing for about 30 seconds; removing hydrophilic and hydrophobic biological fluids upon adherence, leaving the dressing in place at a target tissue site, and allowing the dressing to remain at the target tissue site for 24 hours.

16. The chitosan dressing according to claim 15 for use in the treatment of a gastrointestinal tract bleeding, wherein the dressing dissolves completely without human intervention in one to seven days.

17. The chitosan dressing according to claim 1, wherein the dressing has a chitosan acid salt content of between about 2% and about 15% by weight.

18. The chitosan dressing according to claim 1, wherein the dressing has a degree of catechol substitution of about 20%.

19. The chitosan dressing according to claim 6, wherein the dressing comprising catechol oxidized to o-quinone and cross-linked exhibits good resistance to dissolution and degradation in the upper gastrointestinal tract.

\*   \*   \*   \*   \*